US012620488B2

(12) United States Patent
Bose et al.

(10) Patent No.: US 12,620,488 B2
(45) Date of Patent: May 5, 2026

(54) MACHINE LEARNING ALGORITHM FOR THE DETECTION OF CARDIAC AMYLOIDOSIS FROM 12 LEAD ECG DATA

(71) Applicant: AccurKardia, Inc., New York, NY (US)

(72) Inventors: Sluso Anne Bose, Kerala (IN); Catherine Vinnarasi Antony, Tamil Nadu (IN); Komala T.A, Karnataka (IN); Rozina Moazzam Ali Shaikh, Maharashtra (IN)

( * ) Notice: Subject to any disclaimer, the term of this patent is extended or adjusted under 35 U.S.C. 154(b) by 0 days.

(21) Appl. No.: 18/979,722

(22) Filed: Dec. 13, 2024

(65) Prior Publication Data

US 2025/0201412 A1     Jun. 19, 2025

Related U.S. Application Data

(60) Provisional application No. 63/610,373, filed on Dec. 14, 2023.

(51) Int. Cl.

| | |
|---|---|
| *G16H 50/20* | (2018.01) |
| *A61B 5/352* | (2021.01) |
| *A61B 5/353* | (2021.01) |
| *A61B 5/355* | (2021.01) |
| *A61B 5/36* | (2021.01) |
| *G16H 10/60* | (2018.01) |

(52) U.S. Cl.
CPC ............. *G16H 50/20* (2018.01); *A61B 5/352* (2021.01); *A61B 5/353* (2021.01); *A61B 5/355* (2021.01); *A61B 5/36* (2021.01); *G16H 10/60* (2018.01)

(58) Field of Classification Search
CPC ........ G16H 50/20; G16H 10/60; G16H 50/70; A61B 5/352; A61B 5/353; A61B 5/355; A61B 5/36; A61B 5/7267
See application file for complete search history.

(56) References Cited

U.S. PATENT DOCUMENTS

2022/0386928 A1 * 12/2022 Delgado ................ A61B 5/339

FOREIGN PATENT DOCUMENTS

| | | | | | |
|---|---|---|---|---|---|
| KR | 20220143400 A | * | 10/2022 | ............ | G16H 50/20 |
| WO | 2022251750 A1 | | 1/2022 | | |
| WO | 202226227 A1 | | 10/2022 | | |

OTHER PUBLICATIONS

Lo Iacono et al. (Lo Iacono F, Maragna R, Pontone G and Corino VDA (2023) A robust radiomic-based machine learning approach to detect cardiac amyloidosis using cardiac computed tomography. Front. Radiol. 3:1193046. doi: 10.3389/fradi.2023.1193046), (Year: 2023).*

(Continued)

*Primary Examiner* — Linh Giang Le
(74) *Attorney, Agent, or Firm* — Naira Simmons; Sid Kapoor; Pierson Ferdinand LLP

(57) ABSTRACT

The present disclosure provides systems and methods for detection of cardiac amyloidosis from electrocardiogram (ECG) signals. In particular, the present disclosure identified critical novel features that can be incorporated in systems and methods for the detection of cardiac amyloidosis from one or more ECG signals.

29 Claims, 9 Drawing Sheets

(56) References Cited

OTHER PUBLICATIONS

Francesca Lo Iacono, Riccardo Maragna, Gianluca Pontone, and Valentina D. A. Corino; A robust radiomic-based machine learning approach to detect cardiac amyloidosis using cardiac computed tomography; Frontiers in Radiology; Published Jun. 16, 2023, 12 pages. (doi: 10.3389/fradi.2023.1193046).

Yehualashet Magersa Ayano, Freidhelm Schwenker, Bisrat Derebssa Dufera, Taye Girma Debelee; Interpretable Machine Learning Techniques in ECG-Based Heart Disease Classification: A Systematic Review; Diagnostics 2023, 13, 11; Published Dec. 22, 2022; 37 pages. (https://doi.org/103390/diagnostics 13010111).

International Search Report dated Apr. 11, 2025.

Written Opinion of the International Searching Authority (ISA) dated Apr. 11, 2025.

* cited by examiner

MACHINE LEARNING ALGORITHM FOR THE DETECTION OF CARDIAC AMYLOIDOSIS FROM 12 LEAD ECG DATA

FIELD

The present disclosure relates to systems and processes for detection of cardiac amyloidosis. Cardiac Amyloidosis is a progressive restrictive cardiomyopathy that leads to heart failure and poor patient prognosis. Amyloidosis arises from the mis-folding of precursor proteins that become insoluble and deposit in the tissues, including heart muscle. The vast majority of cardiac amyloid cases result from light chain fibrils deposition (AL Amyloid) or Transthyretin (ATTR Amyloid) deposition.

SUMMARY

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

Cardiac amyloidosis is a protein misfolding disorder involving deposition of amyloid fibril proteins in the heart. The associated fibrosis of the conduction tissue results in conduction abnormalities and arrhythmias. "Classical" electrocardiogram (ECG) findings in cardiac amyloidosis include that of low voltage complexes with increased left ventricular wall thickness on echocardiography. However, this "classical" finding is neither sensitive nor specific. Nor is it consistent: conventional wisdom in recent literature suggests that ECG patterns are inconsistent in cardiac amyloidosis patients. Ng, P. L., Lim, Y. C., Evangelista, L. K., Wong, R. C., Chai, P., Sia, C. H., Loi, H. Y., Yeo, T. C., Lin, W. (2022). See, e.g., utility and pitfalls of the electrocardiogram in the evaluation of cardiac amyloidosis. Annals of Noninvasive Electrocardiology, 27, e12967. See also, Cappelli F, Vignini E, Martone R, Perlini S, Mussinelli R, Sabena A, Morini S, Gabriele M, Taborchi G, Bartolini S, Lossi A, Nardi G, Marchionni N, Di Mario C, Olivotto I, Perfetto F. Baseline ECG Features and Arrhythmic Profile in Transthyretin Versus Light Chain Cardiac Amyloidosis. Circ Heart Fail. 2020. In some aspects, the invention describes systems and processes for detection of cardiac amyloidosis from one or more meticulously selected electrocardiogram (ECG) parameters (i.e., added as features into a machine learning model). The disclosure describes the process for annotation of a large database (approximately 1 million patients) with a label associated with one or more cardiac amyloidosis diagnosis or a negative control non-amyloidosis diagnosis. The designation for the cardiac amyloidosis can be selected from, e.g., the group consisting of: light chain (AL) amyloidosis, transthyretin related (ATTR) amyloidosis, organ limited amyloidosis, lichen amyloidosis, heredofamilial amyloidosis, unspecified amyloidosis, neuropathic heredofamilial amyloidosis, and secondary systemic amyloidosis. Notably, the selection of features including a P wave duration, a P wave amplitude, an R wave duration, an R wave amplitude, an S wave amplitude, a T wave duration, a T wave amplitude, a PR Interval (PRI) value, or a QT value is demonstrated by the disclosure to provide a suitable basis for the development of a system where a feature (or a subset of features) strongly associated with a cardiac amyloidosis designation correctly identifies an ECG from a subject afflicted with cardiac amyloidosis with high sensitivity and specificity.

In some aspects, the disclosure provides, a method for identifying one or more electrocardiogram (ECG) parameters(s) that are informative of cardiac amyloidosis, comprising: annotating a plurality of electrocardiogram (ECG) parameters in a database as associated with one or more cardiac amyloidosis designations or a negative cardiac amyloidosis control designation, whereby the designation for the cardiac amyloidosis is selected from the group consisting of: light chain (AL) amyloidosis, transthyretin related (ATTR) amyloidosis, organ limited amyloidosis, lichen amyloidosis, heredofamilial amyloidosis, unspecified amyloidosis, neuropathic heredofamilial amyloidosis, and secondary systemic amyloidosis; instructing a machine learning model to distinguish the plurality of electrocardiogram (ECG) parameters, wherein the machine learning model is instructed to distinguish one or more parameters selected from a group comprising a P wave duration, a P wave amplitude, an R wave duration, an R wave amplitude, an S wave amplitude, a T wave duration, a T wave amplitude, a PR Interval (PRI) value, and a QT value based on a pattern present in the one or more cardiac amyloidosis designation(s) that is not present in the negative cardiac amyloidosis control; applying a machine learning (e.g., SHAP) analysis to the plurality of distinguished electrocardiogram (ECG) parameters thereby providing a numeric value that represents the contribution of each parameter to the one or more cardiac amyloidosis designation and identifies one or more electrocardiogram (ECG) parameters(s) that are informative of cardiac amyloidosis. The P wave duration can correspond to any P wave from any lead, such as the P wave duration in lead I, the P wave duration in lead II, the P wave duration in lead III, the P wave duration in lead $V_1$, the P wave duration in lead $V_2$, the P wave duration in lead $V_3$, the P wave duration in lead $V_4$, the P wave duration in lead $V_5$, the P wave duration in lead $V_6$, the P wave duration in lead aVF, the P wave duration in lead aVR, or the P wave duration in lead aVL. Similarly, the P wave amplitude can corresponds to the P wave amplitude in any lead, such as the P wave amplitude in lead I, the P wave amplitude in lead II, the P wave amplitude in lead III, the P wave amplitude in lead $V_1$, the P wave amplitude in lead $V_2$, the P wave amplitude in lead $V_3$, the P wave amplitude in lead $V_4$, the P wave amplitude in lead $V_5$, the P wave amplitude in lead $V_6$, the P wave amplitude in lead aVF, the P wave amplitude in lead a VR, or the P wave amplitude in lead a VL. The R wave duration can correspond to any R wave from any lead, such as the R wave duration in lead I, the R wave duration in lead II, the R wave duration in lead III, the R wave duration in lead $V_1$, the R wave duration in lead $V_2$, the R wave duration in lead $V_3$, the R wave duration in lead $V_4$, the R wave duration in lead $V_5$, the R wave duration in lead $V_6$, the R wave duration in lead aVF, the R wave duration in lead aVR, or the R wave duration in lead aVL. Similarly, the R wave amplitude can corresponds to the R wave amplitude in lead I, the R wave amplitude in lead II, the R wave amplitude in lead III, the R wave amplitude in lead $V_1$, the R wave amplitude in lead $V_2$, the R wave amplitude in lead $V_3$, the R wave amplitude in lead $V_4$, the R wave amplitude in lead $V_5$, the R wave amplitude in lead $V_6$, the R wave amplitude in lead aVF, the R wave amplitude in lead aVR, or the R wave amplitude in lead aVL. The S wave amplitude can correspond to the S wave amplitude in lead I, the S wave amplitude in lead II, the S wave amplitude in lead III, the S wave amplitude in lead $V_1$, the S wave amplitude in lead $V_2$, the S wave amplitude in lead $V_3$, the S wave amplitude in lead $V_4$, the S wave amplitude in lead $V_5$, the S wave amplitude in lead $V_6$, the S wave amplitude in lead aVF, the S wave amplitude in lead aVR, or the S wave amplitude in lead aVL. The T wave amplitude can correspond to the T wave amplitude in lead I, the T wave amplitude in lead II, the T wave amplitude in lead III, the T wave amplitude in lead $V_1$, the T wave amplitude in lead $V_2$, the T wave amplitude in lead $V_3$, the T wave amplitude in lead $V_4$, the T wave amplitude in lead $V_5$, the T wave amplitude in lead $V_6$, the T wave amplitude in lead aVF, the T wave amplitude in lead aVR, or the T wave amplitude in lead aVL. The PR interval can be a value in lead I, a value in lead II, a value in lead III, a value in lead $V_1$, a value in lead $V_2$, a value in lead $V_3$, a value in lead $V_4$, a value in lead $V_5$, a value in lead $V_6$, a value in lead aVF, a value in lead aVL, or a value in lead aVR. In preferred instances the machine learning model is a feed forward model instructed to consider inputs from one or more of the leads described above. In some instances, one of the inputs is the age of a person at the time they receive an electrocardiogram and/or ECG.

In some aspects, the disclosure provides a system for detecting cardiac amyloidosis from an electrocardiogram signal(s), the system comprising: an input module receiving the electrocardiogram (ECG) signal from an information source; an analysis module trained to apply logic to identify a cardiac amyloidosis pattern in one or more of: an R wave amplitude in lead $V_5$ of the ECG; an S wave amplitude in lead $V_3$ of the ECG; an R wave amplitude in lead aVL; an R wave amplitude in lead $V_6$; an R wave amplitude in lead $V_4$; an R wave amplitude in lead I; an S wave amplitude in lead $V_1$; and an S wave amplitude in lead $V_2$; and an output module for outputting a binary classification indicative of a cardiac amyloidosis pattern in the ECG signal or a non-cardiac amyloidosis pattern in the ECG signal. In some instances, the analysis module is a feedforward neural network. In some instances, the sensitivity of the model is greater than 90%, greater than 91%, greater than 92%, greater than 93%, greater than 94%, greater than 95%, greater than 96%, greater than 97%, greater than 98%, or greater than 99%. In some instances, the specificity of the model is greater than 90%, greater than 91%, greater than 92%, greater than 93%, greater than 94%, greater than 95%, greater than 96%, greater than 97%, greater than 98%, or greater than 99%. In some instances, the cardiac amyloidosis is selected from the group consisting of: light chain (AL) amyloidosis, transthyretin related (ATTR) amyloidosis, organ limited amyloidosis, lichen amyloidosis, heredofamilial amyloidosis, unspecified amyloidosis, neuropathic heredofamilial amyloidosis, and secondary systemic amyloidosis. In one illustrative model the analysis module was trained to apply logic to identify cardiac amyloidosis on 3000 patients.

These aspects and other features and advantages of the invention are described below in more detail.

Terminology

As used herein, the term "cardiac amyloidosis" or "stiff heart syndrome" or "amyloidosis" refers to a multisystemic condition that occurs when amyloid deposits take the place of normal heart muscle. Herein, cardiac amyloidosis includes distinct types of amyloidosis, which may be caused by different proteins that form amyloid fibrils.

As used herein, the term "transthyretin amyloidosis" or "ATTR amyloidosis" refers to particular type of cardiac amyloidosis. In ATTR, transthyretin, a protein produced in the liver, misfolds and forms amyloid fibrils that build up in the heart or other sites, such as tissues in the wrist or neck, or in the nerves. This means that people with cardiac ATTR amyloidosis may have heart problems, as well as carpal tunnel syndrome or cervical stenosis and/or neuropathy. As used herein the term ATTR amyloidosis refers to two types of ATTR amyloidosis: wild-type ATTR amyloidosis (wt-ATTR) and hereditary ATTR amyloidosis (hATTR). wtATTR is generally associated with aging. hATTR, sometimes known as mutant ATTR amyloidosis, is caused by an inherited genetic mutation in the TTR gene that predisposes the transthyretin protein to misfold.

As used herein, the term "amyloid light-chain amyloidosis" or "AL amyloidosis" refers to particular type of cardiac amyloidosis. AL amyloidosis is generally caused by "light chain" proteins, which are produced by plasma cells in the bone marrow. The amyloid fibrils associated with light-chain proteins can build up in organs and tissues throughout the body, though they tend to deposit in the heart, kidney, liver, tongue, gastrointestinal tract, and peripheral nerves.

As described herein, the expression "cardiac amyloidosis electrical signal" refers to electrocardiogramns of electrical signals from the heart (conduction system) from a subject afflicted with cardiac amyloidosis.

As used herein, electrocardiography is the process of producing an electrocardiogram (ECG or EKG), a recording of the heart's electrical activity through repeated cardiac cycles.

As used herein, "ECG" generally means a 12-lead ECG taken from a subject while lying down. ECG terminology has two meanings for the word "lead": 1) the cable used to connect an electrode to the ECG recorder; and 2) the electrical view of the heart obtained from any one combination of electrodes. A standard ECG uses 10 cables to obtain 12 electrical views of the heart. The different views reflect the angles at which electrodes "look" at the heart and the direction of the heart's electrical depolarization. The electrical activity detected by the electrocardiogram machine is measured in millivolts. ECG machines are calibrated so that a raw signal with an amplitude of 1 mV moves the recording stylus vertically 1 cm. A 12-lead ECG consists of three bipolar limb leads (I, II, and III) (further defined below), the unipolar limb leads (AVR, AVL, and AVF), and six unipolar chest leads, also called precordial or V leads, ($V_1$, $V_2$, $V_3$, $V_4$, $V_5$, and $V_6$).

As used herein, the expression "limb leads" refers to three bipolar leads and three unipolar leads obtained from three electrodes attached to the left arm, the right arm, and the left leg, respectively. They can be abbreviated limb leads I, II, III, IV, V, and VI.

As used herein, the "bipolar limb" or "bipolar limb lead" refers to the potential difference between two of the three limb electrodes (I, II, and III).

As used herein, in some instances, the term "Lead I ECG signals" or "Lead I signals" generally refer to the potential difference between electrodes in the right arm-left arm. It is specifically contemplated that the term "Lead I ECG signal" encompasses intermittent single-lead (Lead I) ECG measurements obtained from a wrist-worn device ("wrist-pulse Lead I ECG signal").

As used herein, the term "Lead II ECG signals" or "Lead II signals" refers to the potential difference between electrodes in the right arm-left leg.

As used herein, the term "Lead III ECG signals" or "Lead III signals" refers to the potential difference between electrodes in the left leg-left arm.

As used herein, "unipolar limb lead" refers to unipolar limb leads IV, V, and VI (AVR, AVL, and AVF).

As used herein, "unipolar chest leads", "precordial leads" or "V leads" refers to V leads, ($V_1$, $V_2$, $V_3$, $V_4$, $V_5$, and $V_6$).

As used herein, the term "P wave" is a small deflection wave that represents atrial depolarization.

As used herein, the term "PR interval" or "PRI interval" is the time between the first deflection of the P wave and the first deflection of the QRS complex.

As used herein, the term "QRS wave complex" refers to three waves of the QRS complex representing ventricular depolarization: if a wave immediately after the P wave is an upward deflection, it is an R wave; if it is a downward deflection, it is a Q wave. Small Q waves correspond to depolarization of the interventricular septum. Q waves can also relate to breathing and are generally small and thin. They can also signal an old myocardial infarction (in which case they are big and wide). The R wave reflects depolarization of the main mass of the ventricles-hence it is frequently the largest wave. The S wave signifies the final depolarization of the ventricles, at the base of the heart.

As used herein, the term "ST segment" or "ST interval", is the time between the end of the QRS complex and the start of the T wave. It reflects the period of zero potential between ventricular depolarization and repolarization.

As used herein, the term "T wave" represents ventricular repolarization (atrial repolarization). This is generally obscured by the large QRS complex wave.

As used herein, the term "feature 1" refers to P wave duration in lead I.

As used herein, the term "feature 2" refers to P wave duration in lead II.

As used herein, the term "feature 3" refers to P wave duration in lead III.

As used herein, the term "feature 4" refers to P wave duration in lead V1.

As used herein, the term "feature 5" refers to P wave duration in lead V2.

As used herein, the term "feature 6" refers to P wave duration in lead V3.

As used herein, the term "feature 7" refers to P wave duration in lead V4.

As used herein, the term "feature 8" refers to P wave duration in lead V5.

As used herein, the term "feature 9" refers to P wave duration in lead V6.

As used herein, the term "feature 10" refers to P wave duration in lead a VF.

As used herein, the term "feature 11" refers to P wave duration in lead a VR.

As used herein, the term "feature 12" refers to P wave duration in lead a VL.

As used herein, the term "feature 13" refers to P wave amplitude in lead I.

As used herein, the term "feature 14" refers to P wave amplitude in lead II.

As used herein, the term "feature 15" refers to P wave amplitude in lead III.

As used herein, the term "feature 16" refers to P wave amplitude in lead V1.

As used herein, the term "feature 17" refers to P wave amplitude in lead V2.

As used herein, the term "feature 18" refers to P wave amplitude in lead V3.

As used herein, the term "feature 19" refers to P wave amplitude in lead V4.

As used herein, the term "feature 20" refers to P wave amplitude in lead V5.

As used herein, the term "feature 21" refers to P wave amplitude in lead V6.

As used herein, the term "feature 22" refers to P wave amplitude in lead aVF.

As used herein, the term "feature 23" refers to P wave amplitude in lead aVR.

As used herein, the term "feature 24" refers to P wave amplitude in lead aVL.

As used herein, the term "feature 25" refers to R wave amplitude in lead I.

As used herein, the term "feature 26" refers to R wave amplitude in lead II.

As used herein, the term "feature 27" refers to R wave amplitude in lead III.

As used herein, the term "feature 28" refers to R wave amplitude in lead V1.

As used herein, the term "feature 29" refers to R wave amplitude in lead V2.

As used herein, the term "feature 30" refers to R wave amplitude in lead V3.

As used herein, the term "feature 31" refers to R wave amplitude in lead V4.

As used herein, the term "feature 32" refers to R wave amplitude in lead V5.

As used herein, the term "feature 33" refers to R wave amplitude in lead V6.

As used herein, the term "feature 34" refers to R wave amplitude in lead aVF.

As used herein, the term "feature 35" refers to R wave amplitude in lead aVR.

As used herein, the term "feature 36" refers to R wave amplitude in lead aVL.

As used herein, the term "feature 37" refers to R wave duration in lead I.

As used herein, the term "feature 38" refers to R wave duration in lead II.

As used herein, the term "feature 39" refers to R wave duration in lead III.

As used herein, the term "feature 40" refers to R wave duration in lead V1.

As used herein, the term "feature 41" refers to R wave duration in lead V2.

As used herein, the term "feature 42" refers to R wave duration in lead V3.

As used herein, the term "feature 43" refers to R wave duration in lead V4.

As used herein, the term "feature 44" refers to R wave duration in lead V5.

As used herein, the term "feature 45" refers to R wave duration in lead V6.

As used herein, the term "feature 46" refers to R wave duration in lead aVF.

As used herein, the term "feature 47" refers to R wave duration in lead aVR.

As used herein, the term "feature 48" refers to R wave duration in lead aVL.

As used herein, the term "feature 49" refers to S wave amplitude in lead I.

As used herein, the term "feature 50" refers to S wave amplitude in lead II.

As used herein, the term "feature 51" refers to S wave amplitude in lead III.

As used herein, the term "feature 52" refers to S wave amplitude in lead V1.

As used herein, the term "feature 53" refers to S wave amplitude in lead V2.

As used herein, the term "feature 54" refers to S wave amplitude in lead V3.

As used herein, the term "feature 55" refers to S wave amplitude in lead V4.

As used herein, the term "feature 56" refers to S wave amplitude in lead V5.

As used herein, the term "feature 57" refers to S wave amplitude in lead V6.

As used herein, the term "feature 58" refers to S wave amplitude in lead aVF.

As used herein, the term "feature 59" refers to S wave amplitude in lead a VR.

As used herein, the term "feature 60" refers to S wave amplitude in lead aVL.

As used herein, the term "feature 61" refers to T wave amplitude in lead I.

As used herein, the term "feature 62" refers to T wave amplitude in lead II.

As used herein, the term "feature 63" refers to T wave amplitude in lead III.

As used herein, the term "feature 64" refers to T wave amplitude in lead V1.

As used herein, the term "feature 65" refers to T wave amplitude in lead V2.

As used herein, the term "feature 66" refers to T wave amplitude in lead V3.

As used herein, the term "feature 67" refers to T wave amplitude in lead V4.

As used herein, the term "feature 68" refers to T wave amplitude in lead V5.

As used herein, the term "feature 69" refers to T wave amplitude in lead V6.

As used herein, the term "feature 70" refers to T wave amplitude in lead a VF.

As used herein, the term "feature 71" refers to T wave amplitude in lead a VR.

As used herein, the term "feature 72" refers to T wave amplitude in lead a VL.

As used herein, the term "feature 73" refers to the PRI value in lead I.

As used herein, the term "feature 74" refers to the PRI value in lead II.

As used herein, the term "feature 75" refers to the PRI value in lead III.

As used herein, the term "feature 76" refers to the PRI value in lead V1.

As used herein, the term "feature 77" refers to the PRI value in lead V2.

As used herein, the term "feature 78" refers to the PRI value in lead V3.

As used herein, the term "feature 79" refers to the PRI value in lead V4.

As used herein, the term "feature 80" refers to the PRI value in lead V5.

As used herein, the term "feature 81" refers to the PRI value in lead V6.

As used herein, the term "feature 82" refers to the PRI value in lead aVF.

As used herein, the term "feature 83" refers to the PRI value in lead aVL.

As used herein, the term "feature 84" refers to the PRI value in lead a VR.

As used herein, the term "feature 85" refers to the QT value.

As used herein, the term "about" and the term "approximately," when used to modify a numeric value, indicate that deviations of up to 10% above and below the numeric value remain within the intended meaning of the recited value.

Designation of a range of values includes all integers within or defining the range, and all subranges defined by integers within the range.

The term "and/or" refers to and encompasses any and all possible combinations of one or more of the associated listed items, as well as the lack of combinations when interpreted in the alternative ("or").

The term "or" refers to any one member of a particular list and also includes any combination of members of that list.

The singular forms of the articles "a," "an," and "the" include plural references unless the context clearly dictates otherwise. For example, the term "a protein" or "at least one protein" can include a plurality of proteins, including mixtures thereof.

Statistically significant means $p \leq 0.05$.

BRIEF DESCRIPTION OF THE DRAWINGS

The foregoing and other features and advantages of the present invention will be more fully understood from the following detailed description of illustrative configurations taken in conjunction with the accompanying drawings in which.

INCORPORATION BY REFERENCE

Figure 1:
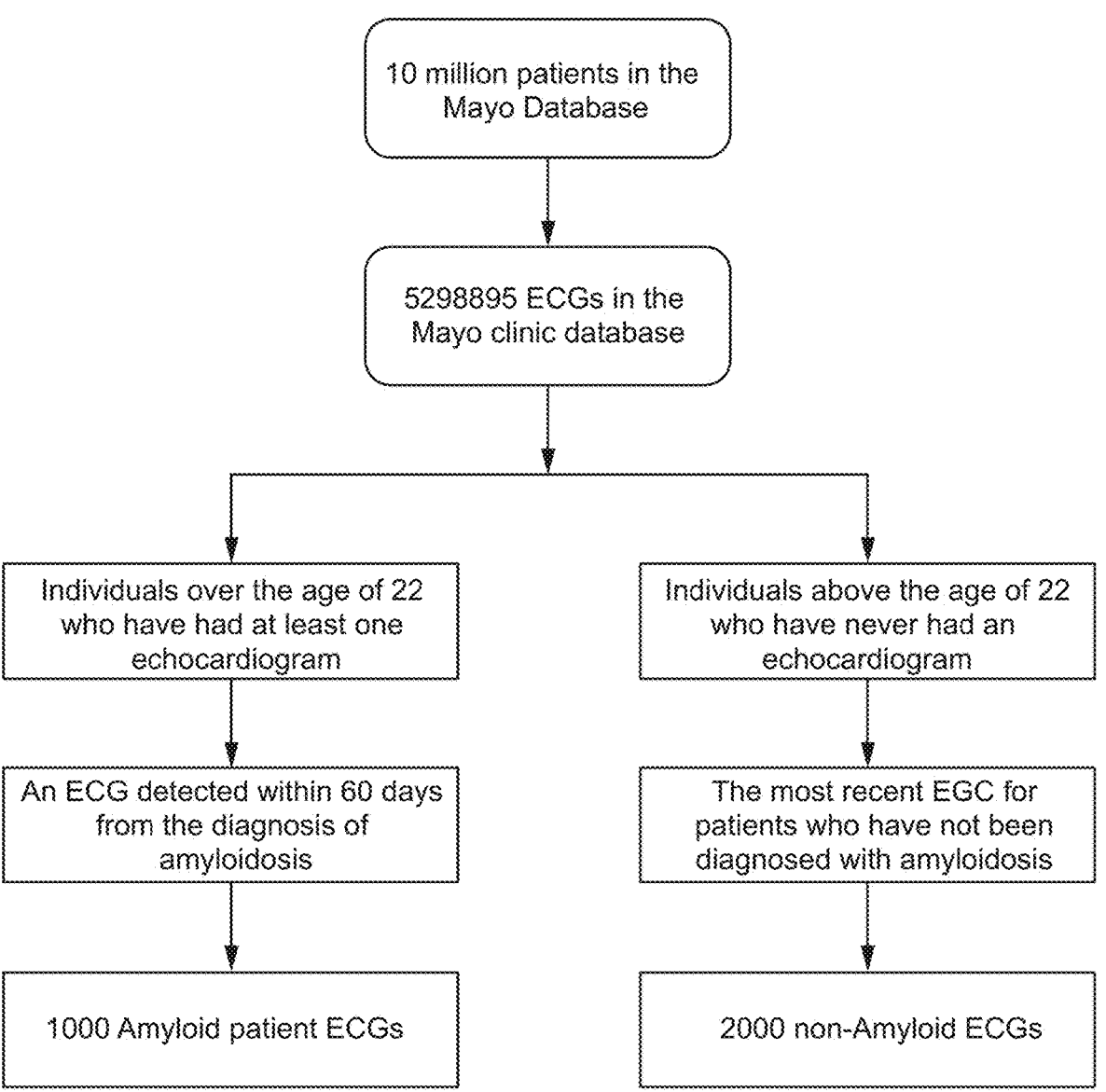
FIG. 1 (FIG. 1) is a flow chart with illustrative steps for developing a model data set.

All publications, patents, and patent applications mentioned in this specification are herein incorporated by reference to the same extent as if each individual publication, patent, or patent application was specifically and individually indicated to be incorporated by reference.

DETAILED DESCRIPTION

I. Overview

All of the functionalities described in connection with one embodiment of the methods, compositions, or formulations described herein are intended to be applicable to the additional configurations of the methods, compositions, or formulations described herein except where expressly stated or where the feature or function is incompatible with the additional configurations. For example, where a given feature or function of component is expressly described in connection with one embodiment but not expressly mentioned in connection with an alternative embodiment, it should be understood that the feature or component may be deployed, utilized, or implemented in connection with the alternative embodiment unless the feature or component is incompatible with the alternative embodiment.

Cardiac Amyloidosis is a progressive restrictive cardiomyopathy that often leads to heart failure and poor patient prognosis. Amyloidosis generally is believed to arise from the mis-folding of precursor proteins that become insoluble and deposit in the tissues, including heart muscle. The vast majority of cardiac amyloid cases result from light chain fibrils deposition (AL Amyloid) or Transthyretin (ATTR Amyloid) deposition, although other types of deposits may cause amyloidosis as well.

AL Amyloid typically arises from haematological plasma cell dyscrasias producing excess light chains. It follows that most existing AL treatments are drawn towards treating the underlying onco-haematological problem, with treatment options including chemotherapies and autologous stem cell transplant. ATTR Amyloid can be hereditary or acquired, with the excess transthyretin proteins being produced in the liver. Liver transplant has traditionally been used as a treatment option for ATTR amyloid. More recently, new treatments such as genetic silencers, stabilizers, and removers have become available.

Notably, the deficiency of suitable, non-surgical, treatment options for cardiac amyloidosis have contributed to a lack of attention to this disorder. The development of prognosis-altering treatments has recently underscored a much felt need for more robust diagnostics, which can in turn provide an overhaul in patient outcomes.

Traditionally, the diagnosis of amyloid formation in cardia tissue conventionally relies on a host if of imaging modalities (e.g., echocardiogram, cardiovascular magnetic resonance (CMR), nuclear scintigraphy). The root cause of the amyloid formation, nonetheless, is caused by a buildup of abnormal proteins in the tissues of the heart that affect its function. Such build-ups may be one cause of failures of aortic stenosis treatments such as transcatheter aortic valve replacement (TAVR). If amyloid formation is correctly identified, a corrective treatment may be prescribed that significantly improves patient outcomes.

Figure 9:
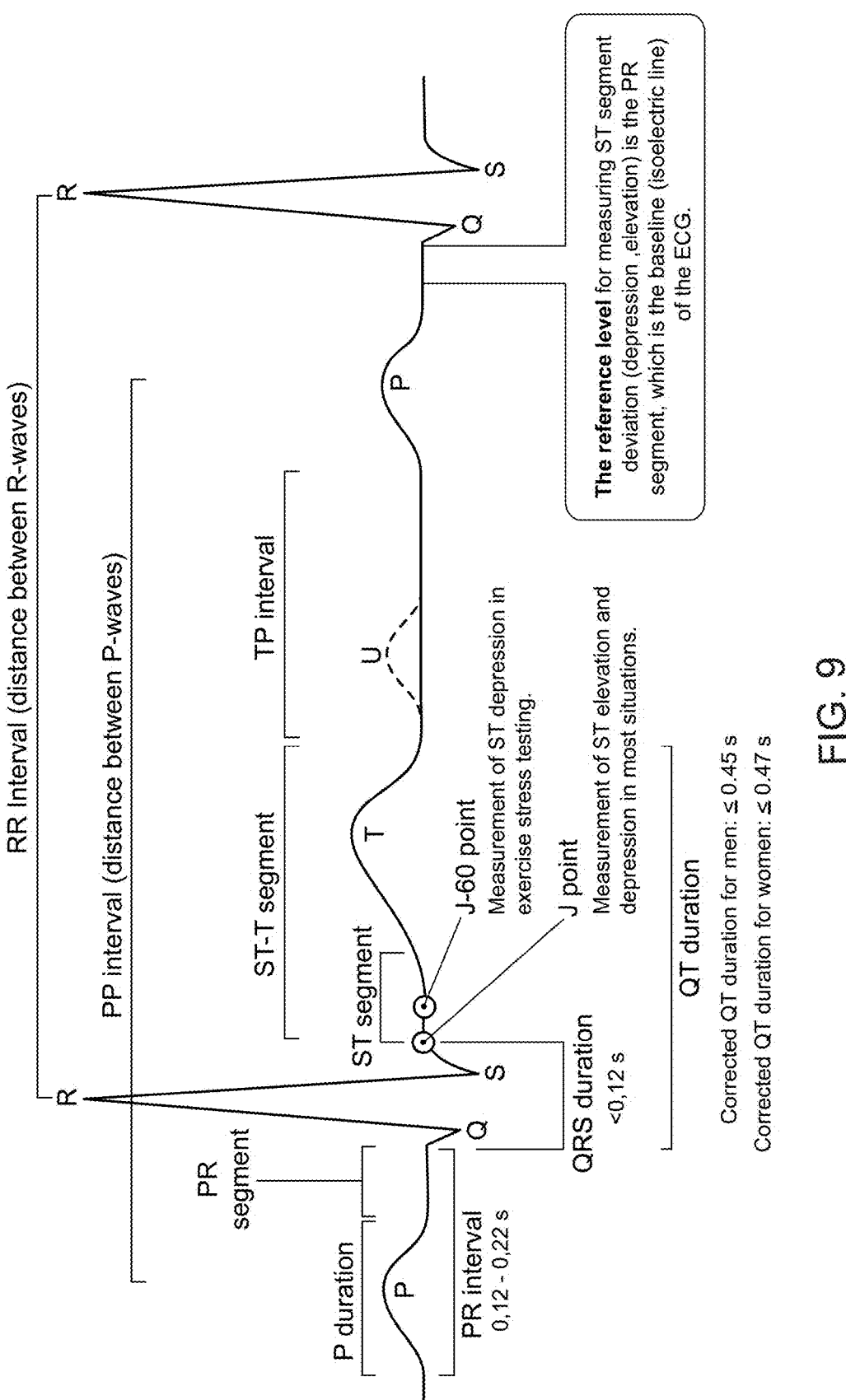
FIG. 9 (FIG. 9) is an schematic illustrating various parameters of an ECG that can be utilized with a method of the disclosure for detecting cardiac a It should be understood that the drawings are not necessarily to scale (e.g., schematics), and that like reference numbers refer to like features.

The present disclosure provides systems and methods for detecting cardiac amyloidosis, caused from light chain fibrils deposition (AL Amyloid), Transthyretin (ATTR Amyloid) deposition, or another build up from electrocardiogram signals. Although abnormalities in ECG parameters, particularly low voltage profiles, have been previously reported in humans afflicted with cardiac amyloidosis patients, the state or art generally concludes that "our main finding is that the electrophysiological profile of CA varies markedly based on its etiology." See, e.g., Circulation: Heart FailureVolume 13, Issue 3, March 2020, quoting main conclusion. Against conventional wisdom, the present disclosure successfully provides a method for identifying one or more electrocardiogram (ECG) parameters(s) that are informative of cardiac amyloidosis by annotating a plurality of electrocardiogram (ECG) parameters, (see FIG. 9 for an schematic of ECG parameters), in a database as associated with one or more cardiac amyloidosis designations or a negative cardiac amyloidosis control designation. An exemplary database was developed by annotating, e.g., parameters described in Table 3 on ECG results, including the age of the subject at the time of testing, with a designation of cardiac amyloidosis vs non-cardiac amyloidosis. An initial database for training was created with the annotated parameter input from approximately 3,000 ECGs of adults (22 yrs and older) who were afflicted with one or more amyloidosis conditions as defined from the ICD codes listed on Table 1. A control group was also established of patients that did not receive a diagnosis (some of the control subjects were deemed healthy and were not subjected to a confirmatory negative echocardiogram; the ECGs however remained available for annotation). Annotation of parameters is distinct from annotation of raw data. The disclosure proceeds to describe the methodology applied to instruct a machine learning model to distinguish the plurality of electrocardiogram (ECG) parameters selected from, e.g., a group comprising a P wave duration, a P wave amplitude, an R wave duration, an R wave amplitude, an S wave amplitude, a T wave duration, a T wave amplitude, a PR Interval (PRI) value, and a QT value based on a pattern present in the one or more cardiac amyloidosis designation(s) that is not present in the negative cardiac amyloidosis control. Suitable ECG parameters are illustrated in FIG. 9. Surprisingly and unexpectedly, the disclosure demonstrates that an analysis of distinguished electrocardiogram (ECG) parameters provides a numeric value that represents the contribution of each parameter to the one or more cardiac amyloidosis designation and identifies one or more electrocardiogram (ECG) parameters(s) that are informative of cardiac amyloidosis.

The disclosure provides a model specifically designed for identifying the presence of amyloid from signals of a plurality (e.g., all 12 lead ECG parameters or substantially all of the parameters) and age of the patient. A system of the disclosure harnesses the information from the ECG parameters with a designed measurement matrix, allowing it to discern distinctive patterns and characteristics that serve as strong indicators for the detection of amyloidosis.

Through its novel analysis, this system and methods of using the same not only detect amyloid but also gains a deep understanding of the data derived from the age and parameters from all the 12 leads of the ECG signal. The model assimilated knowledge from the measurement matrix, honing its ability to recognize and interpret the intricate features that are associated with the presence of amyloidosis, thereby enhancing its diagnostic capabilities.

The disclosure further describes a particular system, which is demonstrated to provide a binary classification indicative of a cardiac amyloidosis pattern in the ECG signal or a non-cardiac amyloidosis pattern in the ECG signal with a sensitivity greater than 90% and a specificity greater than 90%. In some aspects the disclosure provides a system for detecting cardiac amyloidosis from an electrocardiogram signal(s), the system comprising: an input module receiving the electrocardiogram (ECG) signal from an information source; an analysis module trained to apply logic to identify a cardiac amyloidosis pattern in one or more of: an R wave amplitude in lead $V_5$ of the ECG; an S wave amplitude in lead $V_3$ of the ECG; an R wave amplitude in lead aVL; an R wave amplitude in lead $V_6$; an R wave amplitude in lead $V_4$; an R wave amplitude in lead I; an S wave amplitude in lead $V_1$; and an S wave amplitude in lead $V_2$ an output module for outputting a binary classification indicative of a cardiac amyloidosis pattern in the ECG signal or a non-cardiac amyloidosis pattern in the ECG signal.

Further detail is provided below.

II. Processes for Detecting Cardiac Amyloidosis

Cardiac amyloidosis occurs when amyloid deposits take the place of normal heart muscle. It is the most typical type of restrictive cardiomyopathy. Cardiac amyloidosis may affect the way electrical signals move through the heart (conduction system), although to date, conflicting and contradictory reports in the art describe abnormal electrical signals in subjects afflicted with cardiac amyloidosis.

In some aspects the disclosure provides a process for screening for cardiac amyloidosis from an electrocardiogram (ECG) signal. Typically, an ECG instrument records each lead separately, either sequentially or, in some instruments, several leads can be recorded simultaneously. As the stylus moves, depending on the voltage it is reflecting, the recording paper moves at a constant, present speed generally of 25 mm/sec. Hence time is represented on the recording paper by the horizontal axis, and voltage is reflected in the vertical axis. The signal is recorded on a grid, with lines 1 mm apart in both the vertical and horizontal axes. In the horizontal axis, each 1 mm generally represents 0.04 second (40 msec), and every 5 mm, designated by a bold line, indicates 0.2 second. The recording is generally standardized, so that 1 mm vertical deflection reflects 0.1 mV; 5 mm, again indicated by a more bold line, represents 0.5 mV. If the electrocardiogram is recorded at a different paper speed (such as twice the conventional rate) or with a voltage other than the conventional, these alterations must be recorded and taken into account when measuring the various intervals and waves of the ECG. If the electrocardiogram is recorded in a wrist-pulse device these alterations must be taken into account when measuring the various intervals. Notably, the ECG patterns generate various parameters (e.g., parameters illustrated in FIG. 9).

By convention, the first upward deflection from the baseline is termed the P wave, and it reflects atrial depolarization. It is understood that in healthy scenarios, the P wave should not exceed 2.5 mm in height nor 0.11 second in width (i.e., less than three small boxes high and wide). Ventricular depolarization is represented by the QRS complex. The Q wave is the first negative deflection from the baseline after the P wave, but preceding an upward deflection. Normally, the Q wave reflects ventricular septal depolarization, and its duration does not exceed 0.03 second. The R wave is the first positive deflection after the P wave, reflecting depolarization of the ventricular mass. The S wave is the negative deflection following the positive R wave representing later ventricular depolarization. Any positive deflection following an S wave is labeled R' ("R-prime"); any negative deflection following an R' is labeled S'. By convention, an uppercase R or S infers a large deflection, whereas a lowercase r or s infers a smaller deflection. The T wave reflects repolarization of the ventricle and may be represented as either a positive or negative deflection following the QRS complex. The area incorporated within the T wave approximates that within the QRS complex, and its polarity is roughly the same as the principal QRS polarity. Occasionally, another wave, the U wave, may follow the T wave, and it is generally of the same polarity as the T wave. The mechanism of the U wave is unknown, though it may reflect repolarization of papillary muscles, or simply represent an afterpotential. The PR interval is the time from the beginning of the P wave to the beginning of the QRS, whether initiated by a Q or an R, and this interval indicates the time required for the atria to depolarize, and for the electrical current to conduct through the atrioventricular node and bundle branches until the ventricle depolarizes. The QRS interval is that interval from the beginning of the Q wave to the end of the S wave, incorporating ventricular depolarization. The QT interval is the time from the beginning of the Q wave to the end of the T wave, incorporating both ventricular depolarization and repolarization. The PR segment is that portion of the recording between the end of the P wave and the beginning of the QRS. The ST segment is that portion of the recording, generally represented by a horizontal line, from the end of ventricular depolarization, whether represented by an R wave or an S wave, to the beginning of the T wave.

The disclosure describes a novel method and systems for assessing ECG patterns for the presence of characteristics indicative of cardiac amyloidosis consisting of assessments of one or more wave amplitude(s), wave duration, and interval length. In some aspects the disclosure provides a method for identifying one or more electrocardiogram (ECG) parameters(s) that are informative of cardiac amyloidosis, comprising: annotating a plurality of electrocardiogram (ECG) parameters in a database as associated with one or more cardiac amyloidosis designations or a negative cardiac amyloidosis control designation, whereby the designation for the cardiac amyloidosis is selected from the group consisting of: light chain (AL) amyloidosis, transthyretin related (ATTR) amyloidosis, organ limited amyloidosis, lichen amyloidosis, heredofamilial amyloidosis, unspecified amyloidosis, neuropathic heredofamilial amyloidosis, and secondary systemic amyloidosis; instructing a machine learning model to distinguish the plurality of electrocardiogram (ECG) parameters, wherein the machine learning model is instructed to distinguish one or more parameters selected from a group comprising a P wave duration, a P wave amplitude, an R wave duration, an R wave amplitude, an S wave amplitude, a T wave duration, a T wave amplitude, a PR Interval (PRI) value, and a QT value based on a pattern present in the one or more cardiac amyloidosis designation(s) that is not present in the negative cardiac amyloidosis control; applying a SHAP analysis to the plurality of distinguished electrocardiogram (ECG) parameters thereby providing a numeric value that represents the contribution of each parameter to the one or more cardiac amyloidosis designation and identifies one or more electrocardiogram (ECG) parameters(s) that are informative of cardiac amyloidosis. The P wave duration can correspond, e.g., to the P wave duration in lead I, the P wave duration in lead II, the P wave duration in lead III, the P wave duration in lead $V_1$, the P wave duration in lead $V_2$, the P wave duration in lead $V_3$, the P wave duration in lead $V_4$, the P wave duration in lead $V_5$, the P wave duration in lead $V_6$, the P wave duration in lead aVF, the P wave duration in lead a VR, or the P wave duration in lead aVL. The P wave amplitude can correspond to, e.g., the P wave amplitude in lead I, the P wave amplitude in lead II, the P wave amplitude in lead III, the P wave amplitude in lead $V_1$, the P wave amplitude in lead $V_2$, the P wave amplitude in lead $V_3$, the P wave amplitude in lead $V_4$, the P wave amplitude in lead $V_5$, the P wave amplitude in lead $V_6$, the P wave amplitude in lead aVF, the P wave amplitude in lead aVR, or the P wave amplitude in lead aVL. The R wave duration can correspond, e.g., to the R wave duration in lead I, the R wave duration in lead II, the R wave duration in lead III, the R wave duration in lead $V_1$, the R wave duration in lead $V_2$, the R wave duration in lead $V_3$, the R wave duration in lead $V_4$, the R wave duration in lead $V_5$, the R wave duration in lead $V_6$, the R wave duration in lead aVF, the R wave duration in lead aVR, or the R wave duration in lead aVL. The R wave amplitude corresponds to, e.g., the R wave amplitude in lead I, the R wave amplitude in lead II, the R wave amplitude in lead III, the R wave amplitude in lead $V_1$, the R wave amplitude in lead $V_2$, the R wave amplitude in lead $V_3$, the R wave amplitude in lead $V_4$, the R wave amplitude in lead $V_5$, or the R wave amplitude in lead $V_6$, the R wave amplitude in lead aVF, the R wave amplitude in lead aVR, or the R wave amplitude in lead aVL. The S wave amplitude can correspond to, e.g., the S wave amplitude in lead I, the S wave amplitude in lead II, the S wave amplitude in lead III, the S wave amplitude corresponds to the S wave amplitude in lead $V_1$, the S wave amplitude in lead $V_2$, the S wave amplitude in lead $V_3$, the S wave amplitude in lead $V_4$, the S wave amplitude in lead $V_5$, the S wave amplitude in lead $V_6$, the S wave amplitude in lead aVF, the S wave amplitude in lead aVR, or the S wave amplitude in lead aVL. The T wave amplitude corresponds to, e.g., the T wave amplitude in lead I, the T wave amplitude in lead II, the T wave amplitude in lead III, the T wave amplitude in lead $V_1$, the T wave amplitude in lead $V_2$, the T wave amplitude in lead $V_3$, the T wave amplitude in lead $V_4$, the T wave amplitude in lead $V_5$, the T wave amplitude in lead $V_6$, the T wave amplitude in lead aVF, the T wave amplitude in lead aVR, or the T wave amplitude in lead aVL. The PR interval can correspond to, e.g., a value in lead I, a value in lead II, a value in lead III, a value in lead $V_1$, a value in lead $V_2$, a value in lead $V_3$, a value in lead $V_4$, a value in lead $V_5$, a value in lead $V_6$, a value in lead aVF, wherein the PR interval is a value in lead aVL, or a value in lead aVR. In some instances, the machine learning model is a feed forward model, such as the model demonstrated to identify cardiac amyloidosis patterns in the Examples. In some instances, the machine learning model is instructed to consider at least 1 feature, at least 2 features, at least 3 features, at least 4 features, at least 5 features, at least 6 features, at least 7 features, at least 8 features, at least 9 features, at least 10 features, at least 11 features, at least 12 features, at least 13 features, at least 14 features, at least 15 features, at least 16 features, at least 17 features, at least 18 features, at least 19 features, at least 20 features, at least 21 features, at least 22 features, at least 23 features, at least 24 features, at least 25 features, at least 26 features, at least 27 features, at least 28 features, at least 29 features, at least 30 features, at least 31 features, at least 32 features, at least 33 features, at least 34 features, at least 35 features, at least 36 features, at least 37 features, at least 38 features, at least 39 features, at least 40 features, at least 41 features, at least 42 features, at least 43 features, at least 44 features, at least 45 features, at least 46 features, at least 47 features, at least 48 features, at least 49 features, at least 50 features, at least 51 features, at least 52 features, at least 53 features, at least 54 features, at least 55 features, at least 56 features, at least 57 features, at least 58 features, at least 59 features, at least 60 features, at least 61 features, at least 62 features, at least 63 features, at least 64 features, at least 65 features, at least 66 features, at least 67 features, at least 68 features, at least 69 features, at least 70 features, at least 71 features, at least 72 features, at least 73 features, at least 74 features, at least 75 features, at least 76 features, at least 77 features, at least 78 features, at least 79 features, at least 80 features, at least 81 features, at least 82 features, at least 83 features, at least 84 features, at least 85 features, at least 86 features, or another suitable number of features from parameters of lead ECG signals. In some instances, the machine learning model is instructed to distinguish 86 ECG parameters. In some instances the machine learning model receives measurement matrices of the 86 parameters from the database and produces a parameter output between 0 and 1. In specific instances, the machine learning model is instructed to distinguish 86 ECG parameters, specifically the machine learning model receives measurement matrices of one or more of the 86 aforementioned parameters from the database and produces a parameter output between 0 and 1.

The P-Wave, PR Interval and PR Segments in the Assessment of Cardiac Amyloidosis Generally, ECG interpretation traditionally starts with an assessment of the P-wave, which reflects atrial depolarization. The PR interval is the distance between the onset of the P-wave to the onset of the QRS complex. The PR interval typically provides information on whether impulse conduction through the atrioventricular node falls under known standards. The PR segments serves as the baseline (also referred to as the reference line or isoelectric line) of the ECG curve. The amplitude is measured by using the PR segment as the baseline, see, e.g., FIG. 9.

The QRS Complex and its Components, the Q, R, and S Waves in the Assessment of Cardiac Amyloidosis Generally the QRS complex represents depolarization (activation) of the ventricles. It is generally referred to as the "QRS complex" although it may not always display all three waves. Since the electrical vector generated by the left ventricle is many times larger than the vector generated by the right ventricle, the QRS complex is actually a reflection of left ventricular depolarization, factors that make the analysis of a QRS signal complex. In the context of disease, for instance, an R wave or an S wave may not produce standard or readily recognizable signals. QRS duration is the time interval from the onset to end of the QRS complex. Typically, it is understood that a short QRS complex is desirable as it proves that the ventricles are depolarized rapidly, which in turn implies that that the conduction system functions properly. In contrast, wide (also referred to as broad) QRS complexes indicate that ventricular depolarization is slow, which may be due to dysfunction in the conduction system. The disclosure demonstrates that, in the context of cardiac amyloidosis, at least one model can be created where the R wave and S wave produce the most informative signals and can be de-coupled from the broad QRS signals of the art. Further, the disclosure demonstrates that the parameters obtained from certain leads may be informative in a model, but the same parameter obtained from a different lead may not be informative.

The J Point and the ST Segment in the Assessment of Cardia Amyloidosis

The ST segment corresponds to the plateau phase (phase 2) of the action potential. The ST segment is reported to be altered in a wide range of conditions, producing characteristic ST segment changes (e.g., ischemia). There are two types of ST segment deviations. ST segment depression implies that the ST segment is displaced, such that it is below the level of the PR segment. ST segment elevation implies that the ST segment is displaced, such that it is above the level of the PR segment. The magnitude of depression/elevation is measured as the height difference (in millimeters) between the J point and the PR segment. The J point is the point where the ST segment starts. If the baseline (PR segment) is difficult to discern, the TP interval may be used as the reference level.

The T-Wave

The T-wave reflects the rapid repolarization of contractile cells and T-wave changes occur in a wide range of conditions. T-wave changes are frequently misunderstood in clinical practice, which the discussion below will attempt to cure. The transition from the ST segment to the T-wave should be smooth (and not abrupt). The normal T-wave is slightly asymmetric, with a steeper downward slope.

The U-Wave

The U-wave is seen occasionally. It is a positive wave occurring after the T-wave. Its amplitude is generally one-fourth of the T-wave's amplitude. The U-wave is most frequently seen in leads $V_2$-$V_4$. Individuals with prominent T-waves, as well as those with slow heart rates, display U-waves more often. The genesis of the U-wave remains elusive.

QT Interval (Duration) and QTc Interval

QT duration reflects the total duration of ventricular depolarization and repolarization. It is measured from the onset of the QRS complex to the end of the T-wave. The QT duration is inversely related to the heart rate; i.e., the QT interval increases at slower heart rates and decreases at higher heart rates. Therefore, typically, the art teaches that to determine whether the QT interval is within normal limits, it is necessary to adjust for the heart rate. The heart rate-adjusted QT interval is referred to as the corrected QT interval (QTc interval).

The disclosure describes a method in which, through careful conception of input ECG parameters and annotation of a database with information that it does not inherently possess-nor is it able to provide on its own-deep analysis of all 12 parameters of an ECG to discern distinctive patterns and characteristics that serve as strong indicators for the detection of amyloidosis. A system of the disclosure harnessed information embedded within the measurement matrix (see Examples for parameters) and gained a deep understanding of the data derived from the age and parameters of all the 12 leads of a plurality of ECG signals. The dataset encompassed electrocardiograms (ECGs) from a cohort of 10 million patients. Each patient's data profile is characterized by 8 distinct waveforms, aligning with the 8 different leads: I, II, V1, V2, V3, V4, V5, and V6, originally encoded in the base64 format. Each waveform extends across a time span of approximately 10 seconds operating at either 250 or 500 samples per second. The database was annotated a diagnosis code indicative of any form of amyloidosis, and a subset of approximately 3000 patients was used for training. Parameters were trained for binary classification. The model's compilation was configured to use binary cross-entropy loss, the Adam optimizer, and accuracy as the evaluation metric and incorporated two callbacks, one to prevent overfitting by monitoring validation metrics; the other to adjust learning rate.

Such methods and systems identified novel parameters associated with cardiac amyloidosis and provide methods and systems for detection of cardia amyloidosis with a sensitivity greater than 90%, greater than 91%, greater than 92%, greater than 93%, greater than 94%, greater than 95%, greater than 96%, greater than 97%, greater than 98%, and in at least one model with a sensitivity greater than 99%. Similarly, the methods and systems described herein identified novel parameters associated with cardiac amyloidosis and provide methods and systems for detection of cardia amyloidosis with a specificity greater than 90%, greater than 91%, greater than 92%, greater than 93%, greater than 94%, greater than 95%, greater than 96%, greater than 97%, greater than 98%, and in at least one model with a specificity greater than 99%.

Systems for Detecting Cardiac Amyloidosis

In some aspects, the disclosure provides systems and methods for identifying cardiac amyloidosis. The system disclosed herein, or a computer system used in the analyses of one or more features from various waveforms, can share the results with a third-party from any other facility, such as a hospital a clinical facility or another heath care organization. Some systems are configured for detecting, e.g.: a wave duration (e.g., milliseconds, seconds) of a P wave, an R wave, an S wave, a T wave, of one or more of the 12 ECG leads (lead I, lead II, lead III, lead $V_1$, lead $V_2$, lead $V_3$, lead $V_4$, lead $V_5$, lead $V_6$, lead aVF, lead aVR, lead aVL); e.g., a wave amplitude (e.g., 0.1 millimeter to 1 cm and values in between) of a P wave, an R wave, an S wave, a T wave of one or more of the 12 ECG leads (lead I, lead II, lead III, lead $V_1$, lead $V_2$, lead $V_3$, lead $V_4$, lead $V_5$, lead $V_6$, lead aVF, lead aVR, lead aVL); a PR Interval (PRI) value (e.g., milliseconds, seconds), a QT value (e.g., milliseconds, seconds).

A system of the disclosure can comprise a computer operating system configured to perform executable instructions, such as instructions required to, e.g., R-waves, S-waves, P-wave, PR intervals, PR segments, T-wave, U-wave, RR interval, PP interval, ST-T segments, TP interval, QRS duration, R-wave amplitude, S-wave amplitude, QT duration, and other suitable parameters on an ECG.

In some aspects, the disclosure provides a system for detecting cardiac amyloidosis from an electrocardiogram signal(s), the system comprising: an input module receiving the electrocardiogram (ECG) signal from an information source; an analysis module trained to apply logic to identify a cardiac amyloidosis pattern in one or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty-one or more, twenty-two or more, twenty-three or more, twenty-four or more, twenty-five or more, twenty-six or more, twenty-seven or more, twenty-eight or more, twenty-nine or more, thirty or more, thirty-one or more, thirty-two or more, thirty-three or more, thirty-four or more, thirty-five or more, thirty-six or more, thirty-seven or more, thirty-eight or more, thirty-nine or more, forty or more, forty-one or more, forty-two or more, forty-three or more, forty-four or more, forty-five or more, forty-six or more, forty-seven or more, forty-eight or more, forty-nine or more, fifty or more, fifty-one or more, fifty-two or more, fifty-three or more, fifty-four or more, fifty-five or more, fifty-six or more, fifty-seven or more, fifty-eight or more, fifty-nine or more, sixty or more, sixty-one or more, sixty-two or more, sixty-three or more, sixty-four or more, sixty-five or more, sixty-six or more, sixty-seven or more, sixty-eight or more, sixty-nine or more, seventy or more, seventy-one or more, seventy-two or more, seventy-three or more, seventy-four or more, seventy-five or more, seventy-six or more, seventy-seven or more, seventy-eight or more, seventy-nine or more, eighty or more, eighty-one or more, eighty-two or more, eighty-three or more, eighty-four or more, eighty-five or more, eighty-six or more of Patient's age at the time of ECG (in years), P wave duration in lead I, P wave duration in lead II, P wave duration in lead III, P wave duration in lead $V_1$, P wave duration in lead $V_2$, P wave duration in lead $V_3$, P wave duration in lead $V_4$, P wave duration in lead $V_5$, P wave duration in lead $V_6$, P wave duration in lead aVF, P wave duration in lead aVR, P wave duration in lead aVL, P wave amplitude in lead I, P wave amplitude in lead II, P wave amplitude in lead III, P wave amplitude in lead $V_1$, P wave amplitude in lead $V_2$, P wave amplitude in lead $V_3$, P wave amplitude in lead $V_4$, P wave amplitude in lead $V_5$, P wave amplitude in lead $V_6$, P wave amplitude in lead aVF, P wave amplitude in lead aVR, P wave amplitude in lead aVL, R wave amplitude in lead I, R wave amplitude in lead II, R wave amplitude in lead III, R wave amplitude in lead $V_1$, R wave amplitude in lead $V_2$, R wave amplitude in lead $V_3$, R wave amplitude in lead $V_4$, R wave amplitude in lead $V_5$, R wave amplitude in lead $V_6$, R wave amplitude in lead aVF, R wave amplitude in lead aVR, R wave amplitude in lead aVL, R wave duration in lead I, R wave duration in lead II, R wave duration in lead III, R wave duration in lead $V_1$, R wave duration in lead $V_2$, R wave duration in lead $V_3$, R wave duration in lead $V_4$, R wave duration in lead $V_5$, R wave duration in lead $V_6$, R wave duration in lead aVF, R wave duration in lead aVR, R wave duration in lead aVL, S wave amplitude in lead I, S wave amplitude in lead II, S wave amplitude in lead III, S wave amplitude in lead $V_1$, S wave amplitude in lead $V_2$, S wave amplitude in lead $V_3$, S wave amplitude in lead $V_4$, S wave amplitude in lead $V_5$, S wave amplitude in lead $V_6$, S wave amplitude in lead aVF, S wave amplitude in lead aVR, S wave amplitude in lead aVL, T wave amplitude in lead I, T wave amplitude in lead II, T wave amplitude in lead III, T wave amplitude in lead $V_1$, T wave amplitude in lead $V_2$, T wave amplitude in lead $V_3$, T wave amplitude in lead $V_4$, T wave amplitude in lead $V_5$, T wave amplitude in lead $V_6$, T wave amplitude in lead aVF, T wave amplitude in lead aVR, T wave amplitude in lead aVL, PRI value in lead I, PRI value in lead II, PRI value in lead III, PRI value in lead $V_1$, PRI value in lead $V_2$, PRI value in lead $V_3$, PRI value in lead $V_4$, PRI value in lead $V_5$, PRI value in lead $V_6$, PRI value in lead aVF, PRI value in lead aVL, PRI value in lead aVR, and/or a QT value; and an output module for outputting a classification (e.g., binary classification) indicative of a cardiac amyloidosis pattern in the ECG signal or a non-cardiac amyloidosis pattern in the ECG signal. In some instances, the analysis module is a feedforward neural network.

In some aspects, the disclosure provides a system for detecting cardiac amyloidosis from an electrocardiogram signal(s), the system comprising: an input module receiving the electrocardiogram (ECG) signal from an information source; an analysis module trained to apply logic to identify a cardiac amyloidosis pattern in no more than four, no more than five, no more than six, no more than seven, no more than eight, no more than nine, no more than ten, no more than eleven, no more than twelve, no more than thirteen, no more than fourteen, no more than fifteen, no more than sixteen, no more than seventeen, no more than eighteen, no more than nineteen, no more than twenty, no more than twenty-one, no more than twenty-two, no more than twenty-three, no more than twenty-four, no more than twenty-five, no more than twenty-six, no more than twenty-seven, no more than twenty-eight, no more than twenty-nine, no more than thirty, no more than thirty-one, no more than thirty-two, no more than thirty-three, no more than thirty-four, no more than thirty-five, no more than thirty-six, no more than thirty-seven, no more than thirty-eight, no more than thirty-nine, no more than forty, no more than forty-one, no more than forty-two, no more than forty-three, no more than forty-four, no more than forty-five, no more than forty-six, no more than forty-seven, no more than forty-eight, no more than forty-nine, no more than fifty, no more than fifty-one, no more than fifty-two, no more than fifty-three, no more than fifty-four, no more than fifty-five, no more than fifty-six, no more than fifty-seven, no more than fifty-eight, no more than fifty-nine, no more than sixty, no more than sixty-one, no more than sixty-two, no more than sixty-three, no more than sixty-four, no more than sixty-five, no more than sixty-six, no more than sixty-seven, no more than sixty-eight, no more than sixty-nine, no more than seventy, no more than seventy-one, no more than seventy-two, no more than seventy-three, no more than seventy-four, no more than seventy-five, no more than seventy-six, no more than seventy-seven, no more than seventy-eight, no more than seventy-nine, no more than eighty, no more than eighty-one, no more than eighty-two, no more than eighty-three, no more than eighty-four, no more than eighty-five, no more than eighty-six features selected from the group consisting of patient's age at the time of ECG (in years), P wave duration in lead I, P wave duration in lead II, P wave duration in lead III, P wave duration in lead $V_1$, P wave duration in lead $V_2$, P wave duration in lead $V_3$, P wave duration in lead $V_4$, P wave duration in lead $V_5$, P wave duration in lead $V_6$, P wave duration in lead aVF, P wave duration in lead aVR, P wave duration in lead aVL, P wave amplitude in lead I, P wave amplitude in lead II, P wave amplitude in lead III, P wave amplitude in lead $V_1$, P wave amplitude in lead $V_2$, P wave amplitude in lead $V_3$, P wave amplitude in lead $V_4$, P wave amplitude in lead $V_5$, P wave amplitude in lead $V_6$, P wave amplitude in lead aVF, P wave amplitude in lead aVR, P wave amplitude in lead aVL, R wave amplitude in lead I, R wave amplitude in lead II, R wave amplitude in lead III, R wave amplitude in lead $V_1$, R wave amplitude in lead $V_2$, R wave amplitude in lead $V_3$, R wave amplitude in lead $V_4$, R wave amplitude in lead $V_5$, R wave amplitude in lead $V_6$, R wave amplitude in lead aVF, R wave amplitude in lead aVR, R wave amplitude in lead aVL, R wave duration in lead I, R wave duration in lead II, R wave duration in lead III, R wave duration in lead $V_1$, R wave duration in lead $V_2$, R wave duration in lead $V_3$, R wave duration in lead $V_4$, R wave duration in lead $V_5$, R wave duration in lead $V_6$, R wave duration in lead aVF, R wave duration in lead aVR, R wave duration in lead aVL, S wave amplitude in lead I, S wave amplitude in lead II, S wave amplitude in lead III, S wave amplitude in lead $V_1$, S wave amplitude in lead $V_2$, S wave amplitude in lead $V_3$, S wave amplitude in lead $V_4$, S wave amplitude in lead $V_5$, S wave amplitude in lead $V_6$, S wave amplitude in lead aVF, S wave amplitude in lead aVR, S wave amplitude in lead aVL, T wave amplitude in lead I, T wave amplitude in lead II, T wave amplitude in lead III, T wave amplitude in lead $V_1$, T wave amplitude in lead $V_2$, T wave amplitude in lead $V_3$, T wave amplitude in lead $V_4$, T wave amplitude in lead $V_5$, T wave amplitude in lead $V_6$, T wave amplitude in lead aVF, T wave amplitude in lead aVR, T wave amplitude in lead aVL, PRI value in lead I, PRI value in lead II, PRI value in lead III, PRI value in lead $V_1$, PRI value in lead $V_2$, PRI value in lead $V_3$, PRI value in lead $V_4$, PRI value in lead $V_5$, PRI value in lead $V_6$, PRI value in lead aVF, PRI value in lead aVL, PRI value in lead aVR, and/or a QT value; and an output module for outputting a classification (e.g., binary classification) indicative of a cardiac amyloidosis pattern in the ECG signal or a non-cardiac amyloidosis pattern in the ECG signal. In some instances, the analysis module is a feedforward neural network.

In some aspects, a system described herein is optionally connected a computer network. In further configurations, the system is optionally connected to the Internet such that it accesses the World Wide Web, e.g., the reference database of a plurality of normalized waveforms can be stored in the World Wide Web, including normalized waveforms that can provide a binary ("yes or no") identification of cardiac amyloidosis. In some embodiments, it is contemplated that the database comprises a plurality of ECG parameters indicative of a subject afflicted with cardiac amyloidosis, e.g., for the purposes of training a model for detecting cardiac amyloidosis and supporting detection of cardiac amyloidosis. In still further configurations, the system is optionally connected to a cloud computing infrastructure. In other configurations, the digital processing device is optionally connected to an intranet. In other configurations, the digital processing device is optionally connected to a data storage device. In other configurations, the digital processing device could be deployed on premise or remotely deployed in the cloud. In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art. In many aspects, the disclosure contemplates any suitable system that can either be functionally connected with electrocardiogram ECG or EKG equipment, either directly or via a third-party, for on-site monitoring and cardiac amyloidosis classification outputting (e.g., binary classification or a classification associated with a particular type of cardiac amyloidosis).

In some aspects, a system of the disclosure includes an operating system configured to perform executable instructions, e.g., receive via an input module electrocardiogram (ECG) signals from an information source (e.g., an ECG stored in the form of a medical record or a contemporaneous ECG). The operating system is, for example, software, including programs and data, which manages the overall system's hardware and provides services for execution of applications. Those of skill in the art will recognize that suitable server operating systems include, by way of non-limiting examples, FreeBSD, OpenBSD, NetBSD, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some aspects, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. In the specific Examples provided herein, the data was analyzed using IBM SPSS version 24.

In some aspects, a cardiac amyloidosis detection system of the disclosure includes a storage and/or memory device. The storage and/or memory device can be one or more physical apparatuses used to store data or programs on a temporary or permanent basis. In some configurations, the device is volatile memory and requires power to maintain stored information. In some configurations, the device is non-volatile memory and retains stored information when the digital processing device is not powered. In further configurations, the non-volatile memory comprises flash memory. In some configurations, the non-volatile memory comprises dynamic random-access memory (DRAM). In some configurations, the non-volatile memory comprises ferroelectric random access memory (FRAM). In some configurations, the non-volatile memory comprises phase-change random access memory (PRAM). In other configurations, the device is a storage device including, by way of non-limiting examples, CD-ROMs, DVDs, flash memory devices, magnetic disk drives, magnetic tapes drives, optical disk drives, and cloud computing based storage. In further configurations, the storage and/or memory device is a combination of devices such as those disclosed herein.

In some configurations, a cardiac amyloidosis system of the disclosure includes a display to send visual information to a third-party, such as health care facility, a physicians office, or a relative of the subject being monitored for cardiac amyloidosis or undertaking an ECG. In some configurations, the display is a cathode ray tube (CRT). In some configurations, the display is a liquid crystal display (LCD). In further configurations, the display is a thin film transistor liquid crystal display (TFT-LCD). In some configurations, the display is an organic light emitting diode (OLED) display. In various further configurations, on OLED display is a passive-matrix OLED (PMOLED) or active-matrix OLED (AMOLED) display. In some configurations, the display is a plasma display. In other configurations, the display is a video projector. In still further configurations, the display is a combination of devices such as those disclosed herein. In certain configurations the performance of the deep neural network (DNN) in predicting cardiac amyloidosis through a plurality of ECG parameters using one or more of the 12 lead ECG signals is outputted on the display, alongside its respective sensitivity or specificity for that range.

In some configurations, a cardiac amyloidosis detection system includes an input device to receive information from a user. In some configurations, the input device is an electrocardiogram machine, and the cardiac amyloidosis detection system is formatted to receive a plurality of data from electrical activity of the heart as be measured on the surface of the skin, i.e., 12 lead ECG or a wrist-pulse ECG signal. This includes electrocardiogram data from one or more of: 1) RA electrode, placed on the right arm; 2) LA electrode, place on the left arm; 3) RL electrode, placed on the right leg; 4) LL electrode placed on the left leg; 5) $V_1$ electrode, placed in the fourth intercostal space (between ribs 4 and 5); 6) $V_2$ electrode, placed in the fourth intercostal space (between ribs 4 and 5); 7) $V_3$ electrode, placed between leads $V_2$ and $V_4$; 8) $V_4$ electrode, placed in the fifth intercostal space (between ribs 5 and 6); 9) $V_5$ electrode, placed horizontally even with $V_4$; and 10) $V_6$ electrode, placed horizontally even with $V_4$ and $V_5$ in the mid-axillary line. In still further configurations, the input device is a combination of devices such as those disclosed herein. In still further configurations, the input device detects wrist-pulse ECG signal data.

In some configurations, a cardiac amyloidosis detection system includes a digital camera. In some configurations, a digital camera captures digital images, such as, e.g., a schematic representation of a ECG. In some configurations, a digital camera captures still images of the ECG for further analysis by the system, and the system is able to segment the signal.

Non-Transitory Computer Readable Storage Medium

In many aspects, the processes and systems that provide the cardiac amyloidosis detection system disclosed herein include one or more non-transitory computer readable storage media encoded with a program including instructions executable by the operating system of an optionally networked digital processing device. For instance, in some aspects, the processes of the disclosure comprise creating data files associated with a plurality of ECG parameters from a set of data. In certain configurations, the system of the disclosure incorporates a database of normalized waveforms that can be used as a reference. In other configurations, a database of the disclosure may not require a reference database. The non-transitory computer storage medium can store data files associated with one or more 12-lead ECG measurements described herein.

Further the processes and systems that provide the cardiac amyloidosis detection system disclosed herein can include one or more non-transitory computer readable storage media encoded with a program including instructions executable by the operating system of an optionally networked digital processing device configured to create data files associated with a plurality of waveforms (including raw ECG waveforms from one or more 12-lead ECG measurements, and parameters from all 12-lead ECG forms). In preferred configurations, the data is further analyzed by a system of the disclosure comprising a logic model that is trained to apply logic to identify a cardiac amyloidosis pattern in one or more of: an R wave amplitude in lead $V_5$ of the ECG; an S wave amplitude in lead $V_3$ of the ECG; an R wave amplitude in lead aVL; an R wave amplitude in lead $V_6$; an R wave amplitude in lead $V_4$; an R wave amplitude in lead I; an S wave amplitude in lead $V_1$; and an S wave amplitude in lead $V_2$. It is contemplated that slightly different models may identify slightly different parameters. In combination with the analysis of the ECG parameters, the output of the process described herein can provide a differential classification of cardiac amyloidosis based on the diagnosis code. The non-transitory computer storage medium can store data files associated with all of the cardiac amyloidosis designations described herein.

In further configurations, a computer readable storage medium is a tangible component of a system of the disclosure. In still further configurations, a computer readable storage medium is optionally removable from a digital processing device. In some configurations, a computer readable storage medium includes, by way of non-limiting examples, CD-ROMs, DVDs, flash memory devices, solid state memory, magnetic disk drives, magnetic tape drives, optical disk drives, storage area network (SAN), cloud computing systems and services, and the like. In some cases, the program and instructions are permanently, substantially permanently, semi-permanently, or non-transitorily encoded on the media. Such computer readable storage medium is also suitable for storing the set of data contemplated by the disclosure.

Computer Program

The processes and systems that provide the cardiac amyloidosis identification disclosed herein typically include at least one computer program. A computer program includes a sequence of instructions, executable in the digital processing device's CPU, written to perform a specified task. Example 1 provides exemplary steps used by Applicants to, e.g., develop the system and methodology suitable for identification of cardiac amyloidosis from ECG parameters. The examples also demonstrate the sensitivity of an exemplary system. The S-G filter, for instance, is a digital filter that effectively reduces noise and unwanted variations in the signal while preserving the underlying prominent features.

In light of the disclosure provided herein, those of skill in the art will recognize that a computer program may be written in various versions of various languages. In some configurations, a computer program comprises one sequence of instructions. For instance, a program may be written to achieve the same sequence of instructions or substantially the same sequence of instructions instantly described to develop a cardiac amyloidosis model. For instance, in developing the model, the disclosure contemplates systems having computer programs configured to 1) quantify the disparity between the model's predictions and the true binary labels, guiding the optimization process to minimize this discrepancy (e.g., loss='binary_crossentropy'); 2) dynamically updating the model's weights during training (e.g., optimizer='adam': The "optimizer"); 3) measuring the ratio of correctly predicted instances to the total instances (e.g., metrics=['accuracy']); 4) dynamically monitor plateaus during training (e.g., reduce_lr=ReduceLROnPlateau( ); and 5) to prevent overfitting (e.g., early_stopping=EarlyStopping (patience=50, min_delta–0.0001). A program may be written to achieve the same sequence of instructions or substantially the same sequence of instructions instantly described to apply a cardiac amyloidosis detection system to the classification of one or more 12 ECG signals associated with a particular subtype of cardiac amyloidosis.

In some configurations, a computer program instruction is provided from one location (e.g., a computer program that is functionally connected to an ECG apparatus or another medical apparatus). In other configurations, a computer program is provided from a plurality of locations (e.g., ECG signal is provide to a third-party and the analysis occurs in yet another site). In various configurations, a computer program includes one or more software modules. In various configurations, a computer program includes, in part or in whole, one or more web applications, one or more mobile applications, one or more standalone applications, one or more web browser plug-ins, extensions, add-ins, or add-ons, or combinations thereof.

Web Application

In some configurations, the processes and systems that provide the cardiac amyloidosis detection system disclosed herein include a web application. In light of the disclosure provided herein, those of skill in the art will recognize that a web application, in various configurations, utilizes one or more software frameworks and one or more database systems. In some configurations, a web application is created upon a software framework such as Microsoft®.NET or Ruby on Rails (RoR). In some configurations, a web application utilizes one or more database systems including, by way of non-limiting examples, relational, non-relational, object oriented, associative, and XML database systems. In further configurations, suitable relational database systems include, by way of non-limiting examples, Microsoft® SQL Server, mySQL™, and Oracle®. Those of skill in the art will also recognize that a web application, in various configurations, is written in one or more versions of one or more languages. A web application may be written in one or more markup languages, presentation definition languages, client-side scripting languages, server-side coding languages, database query languages, or combinations thereof. In some configurations, a web application is written to some extent in a markup language such as Hypertext Markup Language (HTML), Extensible Hypertext Markup Language (XHTML), or extensible Markup Language (XML). In some configurations, a web application is written to some extent in a presentation definition language such as Cascading Style Sheets (CSS). In some configurations, a web application is written to some extent in a client-side scripting language such as Asynchronous Javascript and XML (AJAX), Flash® Actionscript, Javascript, or Silverlight®. In some configurations, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some configurations, a web application is written to some extent in a database query language such as Structured Query Language (SQL). In some configurations, a web application integrates enterprise server products such as IBM® Lotus Domino®. A web application for providing a career development network for artists that allows artists to upload information and media files, in some configurations, includes a media player element. In various further configurations, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some configurations, the systems that provide the cardiac amyloidosis detection system disclosed herein include a mobile application provided to a mobile digital processing device. In some configurations, the mobile application is provided to a mobile digital processing device at the time it is manufactured. In other configurations, the mobile application is provided to a mobile digital processing device via the computer network described herein. It is specifically contemplated that the cardiac amyloidosis detection system is configured for display on a mobile device. In specific instances, the cardiac amyloidosis detection system outputs a classification result for display on an interface, e.g., graphical user interface. In certain configurations, the cardiac amyloidosis classification output comprises one or a combination of two or more of text, color, imagery, or sound to alert the subject or the technician, physician, or the like administering the ECG of a subject.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some configurations, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB.NET, or combinations thereof. Compilation is often performed, at least in part, to create an executable program. In some configurations, a computer program includes one or more executable complied applications.

Software Modules

The processes and systems that provide the cardiac amyloidosis detection system disclosed herein include, in various configurations, software, server, and database modules. A specific database contemplated by the disclosure is described in the Examples. In view of the disclosure provided herein, software modules are created by techniques known to those of skill in the art using machines, software, and languages known to the art. The software modules disclosed herein are implemented in a multitude of ways. In various configurations, a software module comprises a file, a section of code, a programming object, a programming structure, or combinations thereof. In further various configurations, a software module comprises a plurality of files, a plurality of sections of code, a plurality of programming objects, a plurality of programming structures, or combinations thereof. In various configurations, the one or more software modules comprise, by way of non-limiting examples, a web application, a mobile application, and a standalone application. In some configurations, software modules are in one computer program or application. In other configurations, software modules are in more than one computer program or application. In some configurations, software modules are hosted on one machine. In other configurations, software modules are hosted on more than one machine. In further configurations, software modules are hosted on cloud computing platforms. In some configurations, software modules are hosted on one or more machines in one location. In other configurations, software modules are hosted on one or more machines in more than one location.

Examples

Example 1—Model Development for Cardiac Amyloidosis Detection

This example details the development of a robust model for cardiac amyloidosis detection:

Database Development from 10 Million Patients

The instant model was developed as part of the Mayo Clinic Platform Accelerate program (i.e., "Mayo Clinic Platform_Accelerate Cohort 3 Dataset"). All references to the Mayo clinic below refer to data obtained as part of Applicant's participation in the Accelerate Cohort Program. The data specifically refers to Accelerate Cohort 3 Dataset. As part of this program, Applicant analyzed a dataset encompassing de-identified electrocardiograms (ECGs) from a total of 2.8 million unique patients. The total number of available ECGs was 9.5 million ECG's. Each ECG dataset in the cohort was characterized by 8 distinct waveforms, aligning with the 8 different leads of a traditional ECG: I, II, V1, V2, V3, V4, V5, and V6. These waveforms were originally encoded in the base64 format. Each waveform extended across a time span of 10 seconds operating at either 250 or 500 samples per second. These ECG records were recoded using GE ECG machines. To develop a first cardiac amyloidosis model, Applicant elected to first filter the dataset and to analyze features from 12 Lead ECG signals ("12 Lead Parameters").

For all the ECG data, there is a dedicated table that contains measurements corresponding to each ECG record. This setup supported the retrieval of specific measurements associated with individual ECG records that formed a basis for the selected parameters.

A cohort was created for adult patients at the Mayo Clinic from 1996 to 2022 who are above the age of 22. The patient cohort was carefully selected based on specific criteria to ensure a focused and comprehensive study. To be included in this cohort, patients had to meet two key conditions. Firstly, they must have undergone at least one echocardiogram during their visit to Mayo Hospital. This echocardiogram serves as a critical diagnostic component to assess cardiac health. Secondly, their medical records should contain a diagnosis code indicative of any form of amyloidosis. Amyloidosis is a complex condition characterized by the abnormal accumulation of amyloid protein in various tissues and organs. Meeting both of these conditions ensures that the patients included in this cohort have a strong association with amyloid-related health concerns.

Furthermore, to provide a detailed timeline for analysis, we scrutinized the records of these patients. In cases where a diagnosis of amyloidosis was confirmed, we examined the duration within which this diagnosis was made. Specifically, we focused on the 60-day period around the time of the amyloidosis diagnosis. This timeframe is crucial for understanding the immediate clinical context when amyloidosis was identified.

The table 1 below provides a comprehensive list of the different types of amyloidosis that were included in the training and validation process.

TABLE 1

| Table 1 Amyloidosis ICD codes | |
|---|---|
| CODE | DESCRIPTION |
| E85.4 | Organ limited amyloidosis (HCC), lichen amyloidosis |
| E85.9 | Amyloidosis, unspecified (HCC) |
| 277.3 | AMYLOIDOSIS UNSPECIFIED |
| E85.81 | Light chain (AL) amyloidosis (HCC) |
| 277.39 | Other Amyloidosis, neuropathy peripheral amyloidosis |
| 277.3 | Amyloidosis |
| E85.82 | Wild type transthyretin related (ATTR) amyloidosis (HCC) |
| E85.2 | Heredofamilial amyloidosis, unspecified (HCC) |
| E85.89 | Other Amyloidosis (HCC) |
| E85.8 | Other Amyloidosis |
| E85.1 | Neuropathic heredofamilial amyloidosis (HCC) |
| E85.0 | non - Neuropathic heredofamilial amyloidosis (HCC), amyloidosis myopathy |
| E85.3 | secondary systemic amyloidosis (HCC) |

Concurrently, a control group was chosen to serve as a comparative basis. The control group was established using the same initial cohort of adult patients who sought medical care at the Mayo Clinic between 1996 and 2022 and were aged 22 or older. However, the control group comprises individuals who did not undergo an echocardiogram during their visit to Mayo Clinic.

Furthermore, these patients did not receive a clinical diagnosis of any form of amyloidosis, ensuring that they do not have any known amyloid-related health concerns. To provide a comprehensive comparison, the most recent electrocardiogram (ECG) data was collected for these control group patients.

Model Development

The model was trained on 3000 patients and internally tested using the development data set. FIG. 1 is a flow chart outlining steps describing how the data was curated for development. The baseline characteristics of development set is provided in Table 2 below.

TABLE 2

| | | Training set | |
|---|---|---|---|
| | Overall | Amyloid | Control |
| Patient Count | 3000 | n = 1000 | n = 2000 |
| Gender | | | |
| Male | 1545 (51.5%) | 687 (69%) | 858 (43%) |
| Female | 1455 (48.5%) | 313 (31%) | 1142 (57%) |
| Age (Mean) | 59.2 | 64.6 | 53.8 |
| 22-60 | 1598 (53.27%) | 325 (33.5%) | 1273 (63%) |
| 61-70 | 801 (26.7%) | 350 (35%) | 451 (23%) |
| 71-80 | 472 (15.74%) | 240 (24%) | 233 (12%) |
| 81+ | 128 (4.27%) | 85 (8.5%) | 43 (2%) |
| Ethnicity | | | |
| White | 2704 (90.14%) | 879 (88%) | 1825 (91%) |
| Black | 129 (4.3%) | 77 (8%) | 52 (3%) |

TABLE 2-continued

| | Overall | Amyloid | Control |
|---|---|---|---|
| | | Training set | |
| Asian | 52 (1.73%) | 17 (1%) | 35 (2%) |
| Others | 115 (3.83%) | 27 (3%) | 88 (4%) |

Table 2 provides an overview of the patient demographics within the development dataset. A sample of 3000 was collected for training. In this dataset 51% of the patients were identified as male and 48% as female. The data collection process spanned through all the mayo hospitals including Rochester, Arizona, Florida, and Mayo clinic hospital system (MCHS). The mean age for the training set was 64 years for patients with amyloidosis and 53.8 years for patients without amyloidosis.

Model Training

The model was trained on 3000 patients (see Table 2). The training dataset comprises measurement matrices collected from all 12-lead ECG recordings. The training process involved leveraging labelled data from Mayo clinic to enable accurate detection and analysis of the desired patterns in the ECG signals related with amyloid.

The table below displays the parameters that were supplied to the model in a specific sequence. There are 86 parameters which are fed to the model which includes age of the patients, P wave duration, P wave amplitude, R wave amplitude, R wave duration, S wave amplitude, S wave duration, T wave amplitude and PRI duration of all the 12 leads and average QT. Table 3 describes features personally selected for building of the model.

TABLE 3

| | Parameters | Description |
|---|---|---|
| Feature 0 | NFER AGE | Patient's age at the time of ECG (in years) |
| Feature 1 | P D I | P wave duration in lead I |
| Feature 2 | P D II | P wave duration in lead II |
| Feature 3 | P D III | P wave duration in lead III |
| Feature 4 | P D VI | P wave duration in lead V1 |
| Feature 5 | P D V2 | P wave duration in lead V2 |
| Feature 6 | P D V3 | P wave duration in lead V3 |
| Feature 7 | P D V4 | P wave duration in lead V4 |
| Feature 8 | P D V5 | P wave duration in lead V5 |
| Feature 9 | P D V6 | P wave duration in lead V6 |
| Feature 10 | P D aVF | P wave duration in lead aVF |
| Feature 11 | P D aVR | P wave duration in lead aVR |
| Feature 12 | P D aVL | P wave duration in lead aVL |
| Feature 13 | P A I | P wave amplitude in lead I |
| Feature 14 | P A II | P wave amplitude in lead II |
| Feature 15 | P A III | P wave amplitude in lead III |
| Feature 16 | P A VI | P wave amplitude in lead V1 |
| Feature 17 | P A V2 | P wave amplitude in lead V2 |
| Feature 18 | P A V3 | P wave amplitude in lead V3 |
| Feature 19 | P A V4 | P wave amplitude in lead V4 |
| Feature 20 | P A V5 | P wave amplitude in lead V5 |
| Feature 21 | P A V6 | P wave amplitude in lead V6 |
| Feature 22 | P A aVF | P wave amplitude in lead aVF |
| Feature 23 | P A aVR | P wave amplitude in lead aVR |
| Feature 24 | P A aVL | P wave amplitude in lead aVL |
| Feature 25 | R A I | R wave amplitude in lead I |
| Feature 26 | R A II | R wave amplitude in lead II |
| Feature 27 | R A III | R wave amplitude in lead III |
| Feature 28 | R A VI | R wave amplitude in lead V1 |
| Feature 29 | R A V2 | R wave amplitude in lead V2 |
| Feature 30 | R A V3 | R wave amplitude in lead V3 |
| Feature 31 | R A V4 | R wave amplitude in lead V4 |
| Feature 32 | R A V5 | R wave amplitude in lead V5 |
| Feature 33 | R A V6 | R wave amplitude in lead V6 |

TABLE 3-continued

| | Parameters | Description |
|---|---|---|
| Feature 34 | R A aVF | R wave amplitude in lead aVF |
| Feature 35 | R A aVR | R wave amplitude in lead aVR |
| Feature 36 | R A aVL | R wave amplitude in lead aVL |
| Feature 37 | R D I | R wave duration in lead I |
| Feature 38 | R D II | R wave duration in lead II |
| Feature 39 | R D III | R wave duration in lead III |
| Feature 40 | R D VI | R wave duration in lead V1 |
| Feature 41 | R D V2 | R wave duration in lead V2 |
| Feature 42 | R D V3 | R wave duration in lead V3 |
| Feature 43 | R D V4 | R wave duration in lead V4 |
| Feature 44 | R D V5 | R wave duration in lead V5 |
| Feature 45 | R D V6 | R wave duration in lead V6 |
| Feature 46 | R D aVF | R wave duration in lead aVF |
| Feature 47 | R D aVR | R wave duration in lead aVR |
| Feature 48 | R D aVL | R wave duration in lead aVL |
| Feature 49 | S A I | S wave amplitude in lead I |
| Feature 50 | S A II | S wave amplitude in lead II |
| Feature 51 | S A III | S wave amplitude in lead III |
| Feature 52 | S A VI | S wave amplitude in lead V1 |
| Feature 53 | S A V2 | S wave amplitude in lead V2 |
| Feature 54 | S A V3 | S wave amplitude in lead V3 |
| Feature 55 | S A V4 | S wave amplitude in lead V4 |
| Feature 56 | S A V5 | S wave amplitude in lead V5 |
| Feature 57 | S A V6 | S wave amplitude in lead V6 |
| Feature 58 | S A aVF | S wave amplitude in lead aVF |
| Feature 59 | S A aVR | S wave amplitude in lead aVR |
| Feature 60 | S A aVL | S wave amplitude in lead aVL |
| Feature 61 | T A I | T wave amplitude in lead I |
| Feature 62 | T A II | T wave amplitude in lead II |
| Feature 63 | T A III | T wave amplitude in lead III |
| Feature 64 | T A VI | T wave amplitude in lead V1 |
| Feature 65 | T A V2 | T wave amplitude in lead V2 |
| Feature 66 | T A V3 | T wave amplitude in lead V3 |
| Feature 67 | T A V4 | T wave amplitude in lead V4 |
| Feature 68 | T A V5 | T wave amplitude in lead V5 |
| Feature 69 | T A V6 | T wave amplitude in lead V6 |
| Feature 70 | T A aVF | T wave amplitude in lead aVF |
| Feature 71 | T A aVR | T wave amplitude in lead aVR |
| Feature 72 | T A aVL | T wave amplitude in lead aVL |
| Feature 73 | PRI I | PRI value in lead I |
| Feature 74 | PRI II | PRI value in lead II |
| Feature 75 | PRI III | PRI value in lead III |
| Feature 76 | PRI VI | PRI value in lead V1 |
| Feature 77 | PRI V2 | PRI value in lead V2 |
| Feature 78 | PRI V3 | PRI value in lead V3 |
| Feature 79 | PRI V4 | PRI value in lead V4 |
| Feature 80 | PRI V5 | PRI value in lead V5 |
| Feature 81 | PRI V6 | PRI value in lead V6 |
| Feature 82 | PRI aVF | PRI value in lead aVF |
| Feature 83 | PRI aVR | PRI value in lead aVL |
| Feature 84 | PRI aVL | PRI value in lead aVR |
| Feature 85 | QT | QT value |

The parameters are trained for binary classification. The model's compilation is configured to use binary cross-entropy loss, the Adam optimizer, and accuracy as the evaluation metric. The training process incorporates two essential callbacks. The ReduceLROnPlateau callback adjusts the learning rate dynamically based on the plateauing of a monitored metric, which can aid in smoother convergence. The EarlyStopping callback prevents overfitting by monitoring validation metrics; if no significant improvement occurs within a defined patience period, training halts. The model is then trained for 1000 epochs with these callbacks guiding the process to enhance efficiency and prevent overfitting.

The below code shows the snippet for training.

```
model.compile(loss='binary_crossentropy',
    optimizer='adam', metrics=['accuracy'])
reduce_Ir=ReduceLROnPLATEAU( )
early_stopping=EarlyStopping(patience=50,
    min_delta=0.0001)
model.fit(x,y,epochs=1000,validation_data,    callbacks=
    [reduce_Ir,early_stopping]
``` loss='binary_crossentropy': This parameter specifies the loss function that the model will use during training. In this case, "binary_crossentropy" is employed. This is a suitable choice for binary classification tasks, as it quantifies the disparity between the model's predictions and the true binary labels, guiding the optimization process to minimize this discrepancy.

optimizer='adam': The "optimizer" parameter designates the optimization algorithm responsible for updating the model's weights during training. Here, the Adam optimizer is utilized. Adam adapts the learning rate individually for each parameter, offering a dynamic approach that balances stability and speed in weight updates. This aids in expediting convergence while mitigating the chances of getting stuck in local minima.

metrics=['accuracy']: This parameter specifies the evaluation metric(s) used to assess the model's performance during and after training. In this case, "accuracy" is chosen. Accuracy measures the ratio of correctly predicted instances to the total instances, providing insight into the model's ability to make correct binary classifications.

reduce_lr=ReduceLROnPlateau( ) This callback monitors a specific metric (typically validation loss) during training. If the monitored metric plateaus for a specified number of epochs, the callback reduces the learning rate. This dynamic adjustment aims to aid convergence when progress becomes stagnant, allowing the model to fine-tune its behaviour as it approaches a potential optimal solution.

early_stopping=EarlyStopping (patience=50, min_delta–0.0001): The EarlyStopping callback is employed to prevent overfitting. It watches a chosen validation metric and halts training if the metric fails to demonstrate significant improvement over a certain number of epochs, indicated by the "patience" parameter. The "min_delta" parameter determines the minimal change in the monitored metric that qualifies as an improvement, setting a threshold.

model.fit(x, y, validation_data epochs=1000, callbacks=[reduce_lr, early_stopping]): The fit function initiates the training process. It takes in the pre-processed input data x and target labels y. The "epochs" parameter specifies the number of training iterations. The "callbacks" parameter is used to provide the callbacks created earlier, namely reduce_lr and early_stopping. These callbacks come into play during training to adjust the learning rate and possibly halt training early based on predefined conditions, ultimately enhancing the model's convergence and generalization.

After the training process is complete, the final set of weights, representing the weights acquired by the model during training, are saved. These saved weights can be easily loaded and utilized by the system for any further analysis of the amyloid detection.

Although the weights can change from being trained in slightly different models or from changes in the number of datapoints used to train a model; suitable weights were observed in our model with training of the parameters/ features described in Table 3. It is contemplated that any changes in the number of parameters used to train a model would produce different weights.

Some features appear to be more informative than others. The weights are thus likely to be applicable to each model created and the number of parameters selected.

Example 2—Model System Architecture for Cardiac Amyloidosis Detection

This example illustrates the architecture of a model system validated for cardiac amyloidosis detection.

The disclosure designed an amyloidosis model within a feedforward neural network, a fundamental and versatile architecture often used for various machine learning tasks, particularly with structured or tabular data. This network consists of multiple fully connected layers (referred to as Dense layers in Keras), which play a crucial role in capturing complex patterns and relationships within the input data.

The inventors selected specific features not inputted by any machined and conceived the selection of overall components of the network, including the conception of the ECG parameter inputs. Each component in the network serves a specific purpose. The input layer ('inputs') serves as the entry point for the data, with its shape determined by the number of features in the input dataset. The following hidden layers ('FC1', 'FC2', 'FC3') are responsible for processing and transforming the data. These layers are characterized by their fully connected nature, meaning each neuron is connected to every neuron in the previous and subsequent layers.

To enhance training stability and convergence, batch normalization ('BC1', 'BC2', 'BC3') is applied after each fully connected layer. Batch normalization helps to mitigate issues like vanishing or exploding gradients by standardizing the input to each layer, making the training process more efficient. Furthermore, the Rectified Linear Unit (ReLU) activation functions ('Activation1', 'Activation2') introduce non-linearity, enabling the network to model complex, non-linear relationships in the data. The inclusion of dropout layers ('Dropout1', 'Dropout2', 'Dropout3') with a dropout rate of 0.3 after some of the hidden layers is intended to prevent overfitting. Dropout randomly deactivates a fraction of neurons during training, promoting better generalization to unseen data.

Figure 2:
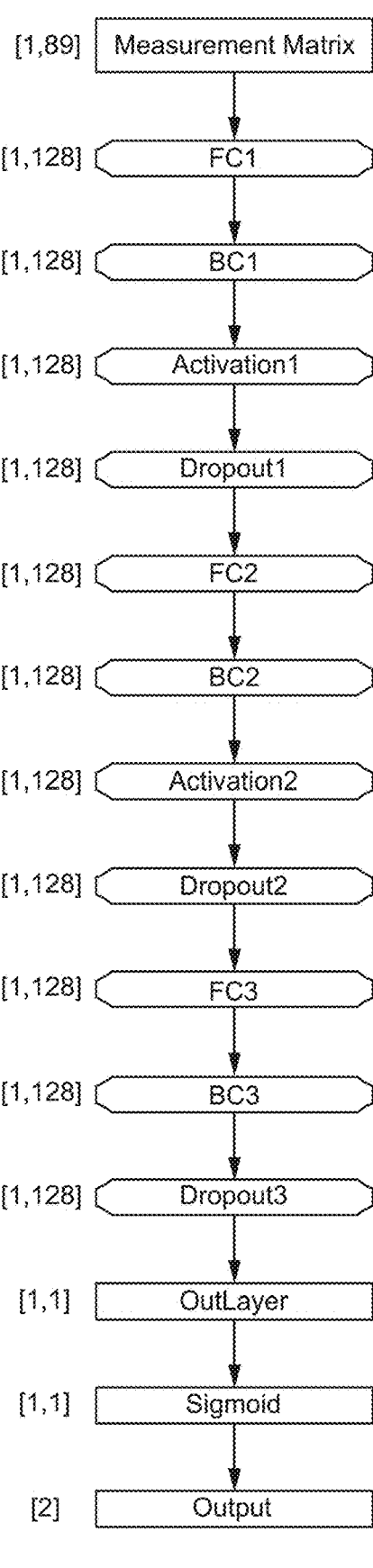
FIG. 2 (FIG. 2) is a flow chart with illustrative steps of a feed-forward neural network.

The final layer ('OutLayer') plays a significant role in the model's goal, which is binary classification. This fully connected layer produces a single output, which is then passed through a sigmoid activation function ('sigmoid'). The sigmoid function squashes the output into the range [0, 1], making it suitable for binary classification tasks. The output represents the predicted probability of the input data belonging to the positive class (1). FIG. 2 is a flow chart with illustrative steps of the system described above (e.g., a feed-forward neural network).

The table below summarizes the details of the model:

TABLE 4

| Layer Name | Output Shape | Parameters |
|---|---|---|
| Inputs | [(None, 86)] | 0 |
| FC1 | (None, 128) | 11136 |
| BC1 | (None, 128) | 512 |
| Activation1 | (None, 128) | 0 |
| Dropout1 | (None, 128) | 0 |
| FC2 | (None, 128) | 16512 |
| BC2 | (None, 128) | 512 |
| Activation2 | (None, 128) | 0 |
| Dropout2 | (None, 128) | 0 |
| FC3 | (None, 128) | 16512 |
| BC3 | (None, 128) | 512 |
| Dropout3 | (None, 128) | 0 |
| OutLayer | (None, 1) | 129 |
| Sigmoid | (None, 1) | 0 |

The model architecture has 14 layers and 45825 parameters. The network function receives measurement matrices of 86 parameters and produces a parameter output between 0 and 1. The figure above shows the feed forward model architecture designed in the instant disclosure for cardiac amyloid detection.

2.1 Model Explainability

SHAP (SHapley Additive explanations) is a powerful tool for explaining the predictions of machine learning models, including neural networks. It provides insights into how specific features influence the model's output and helps to interpret the black-box nature of complex models.

This technique can shed light on the often complex and nonlinear relationships within such neural networks, making them more interpretable and actionable. SHAP operates by providing SHAP values for each feature in the dataset. For a given prediction, SHAP values represent the contribution of each feature to the prediction compared to the average prediction across all possible subsets of features. In the context of this feedforward neural network, SHAP values reveals how specific neurons in the layers respond to input features and how these responses propagate through the network. This information helps to identify which features play (in lead V5) a more significant role in driving the model's decisions, providing valuable insights for feature selection, model fine-tuning, and understanding the neural network's inner workings.

The magnitude (absolute value) of the mean SHAP value reflects the strength of the feature's impact. A larger magnitude indicates a stronger influence on the model's predictions. The SHAP analysis has provided valuable insights into the impact of various features on the model's predictions. It is evident that among the multitude of features, five in particular stand out as the most influential in shaping the model's output. These five features, namely Feature 32 (corresponding to the R wave amplitude in lead V5), Feature 54 (corresponding to S wave amplitude in lead V3), Feature 36 (corresponding to the R wave amplitude in lead aVL), Feature 33 (corresponding to R wave amplitude in lead V6), and Feature 31 (corresponding to the R wave amplitude in lead V4), have consistently demonstrated the highest degree of influence across the dataset. This conclusion is based on the mean SHAP values associated with these features, which serve as a quantitative measure of their average impact on the model's predictions.

Figure 3:
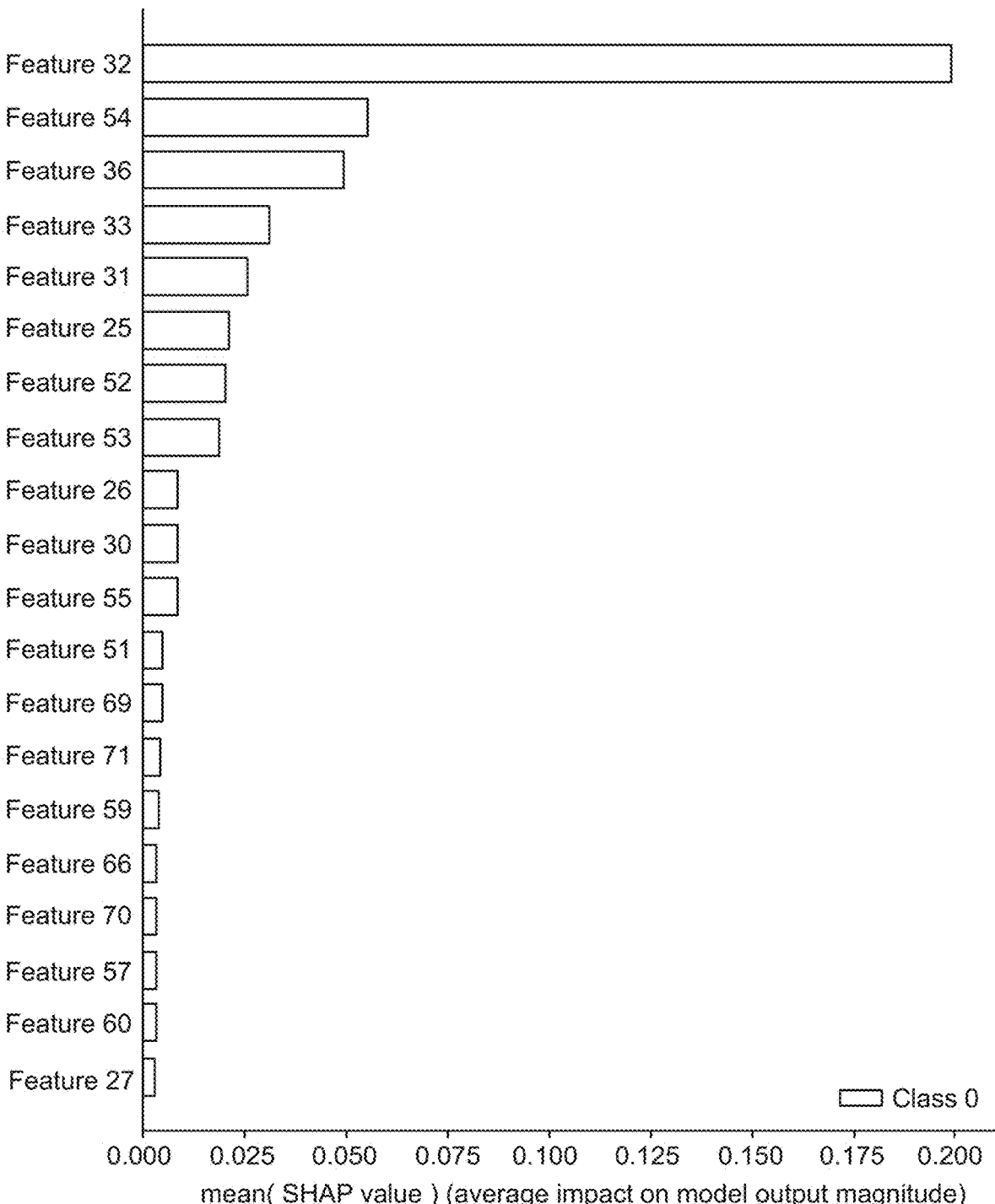
FIG. 3 (FIG. 3) is a chart illustrating a mean SHAP value (average impact on model magnitude).

Among these impactful features, Feature 32 stands out as the most influential, as it boasts the highest mean SHAP value of 0.2. This means that, on average, Feature 32 has a significant positive effect on the model's output magnitude. In practical terms, this indicates that when Feature 32 exhibits higher values or specific patterns, it consistently exerts a substantial positive influence on the model's predictions. FIG. 3 is a chart illustrating the discovery of Feature 32, which corresponds to R wave amplitude in lead V5 as the most informative feature of the model.

2.2 Model Validation

The validation dataset was meticulously curated from a repository of ECG recordings of adult patients receiving medical care at the Mayo Clinic over a substantial period, spanning from 1996 to 2022. The dataset specifically focuses on patients who meet distinct criteria and showcases the outcomes of a comprehensive study. Within this cohort, the disclosure describes discoveries made from an analysis of patients aged 22 and above who exhibited signs of amyloidosis.

To ensure the dataset's quality and relevance, two fundamental conditions were imposed for patient inclusion. Firstly, patients had to have undergone at least one echocardiogram during their visit to Mayo Hospital. This echocardiogram is a pivotal diagnostic tool for evaluating the health of the heart. Secondly, their medical records needed to contain a diagnostic code that indicated the presence of any form of amyloidosis, ensuring that patients with potential cardiac health issues related to amyloidosis were included.

This validation dataset consists of the remaining 912 patients with amyloidosis who were not utilized in the model training phase. Within the selected dataset, a noteworthy 3.95% of cases are attributed to wild-type transthyretin (ATTR) amyloidosis. This variant of amyloidosis, often referred to as wild-type, is recognized for its unique characteristics and is associated with mis-function of the transthyretin protein, primarily affecting the heart and other vital organs. This specific subset of amyloidosis is characterized by the deposition of abnormal ATTR protein, contributing to distinct clinical features and requiring specialized diagnostic and therapeutic approaches.

Additionally, a substantial 15% of cases within the dataset are represented by light chain (AL) amyloidosis. AL amyloidosis is a distinctive form of the disease where abnormal immunoglobulin light chains are deposited in various tissues and organs, leading to a range of clinical manifestations. The inclusion of AL amyloidosis within the dataset adds a layer of complexity and underscores the importance of precise differentiation and targeted management strategies to address the diverse spectrum of amyloidosis presentations and their impact on patient care.

In order to establish a comparative basis for the study, control groups were meticulously selected. The control group was derived from the same initial cohort of adult patients who sought medical care at the Mayo Clinic over the period spanning from 1996 to 2022, and who were aged 22 or older. However, the control group is distinctly characterized by specific attributes. First, the control group comprises individuals who did not undergo an echocardiogram during their visit to the Mayo Clinic. Additionally and importantly, these patients did not receive a clinical diagnosis of any form of amyloidosis. This careful selection process ensures that the control group consists of individuals without any known health concerns related to amyloidosis. The control group comprises individuals who have not received a clinical diagnosis of amyloidosis and have never undergone an echocardiogram, but have an ECG taken. To enable a comprehensive comparison, the most recent electrocardiogram (ECG) data was collected for these control group patients. This allows for a thorough evaluation of the differences and patterns between patients with amyloid-related health concerns and those without, providing valuable insights for the study. 251786 patients were selected in this control group for validation.

An additional dataset was assembled, focusing on a distinct group of 2500 patients diagnosed with aortic valve stenosis. These patients were meticulously selected based on specific criteria, primarily including individuals who are aged 60 years and above. Furthermore, an essential component of the dataset compilation process was ensuring that each patient had undergone both echocardiography (echo) and electrocardiography (ECG) procedures within a 60-day timeframe.

Figure 4:
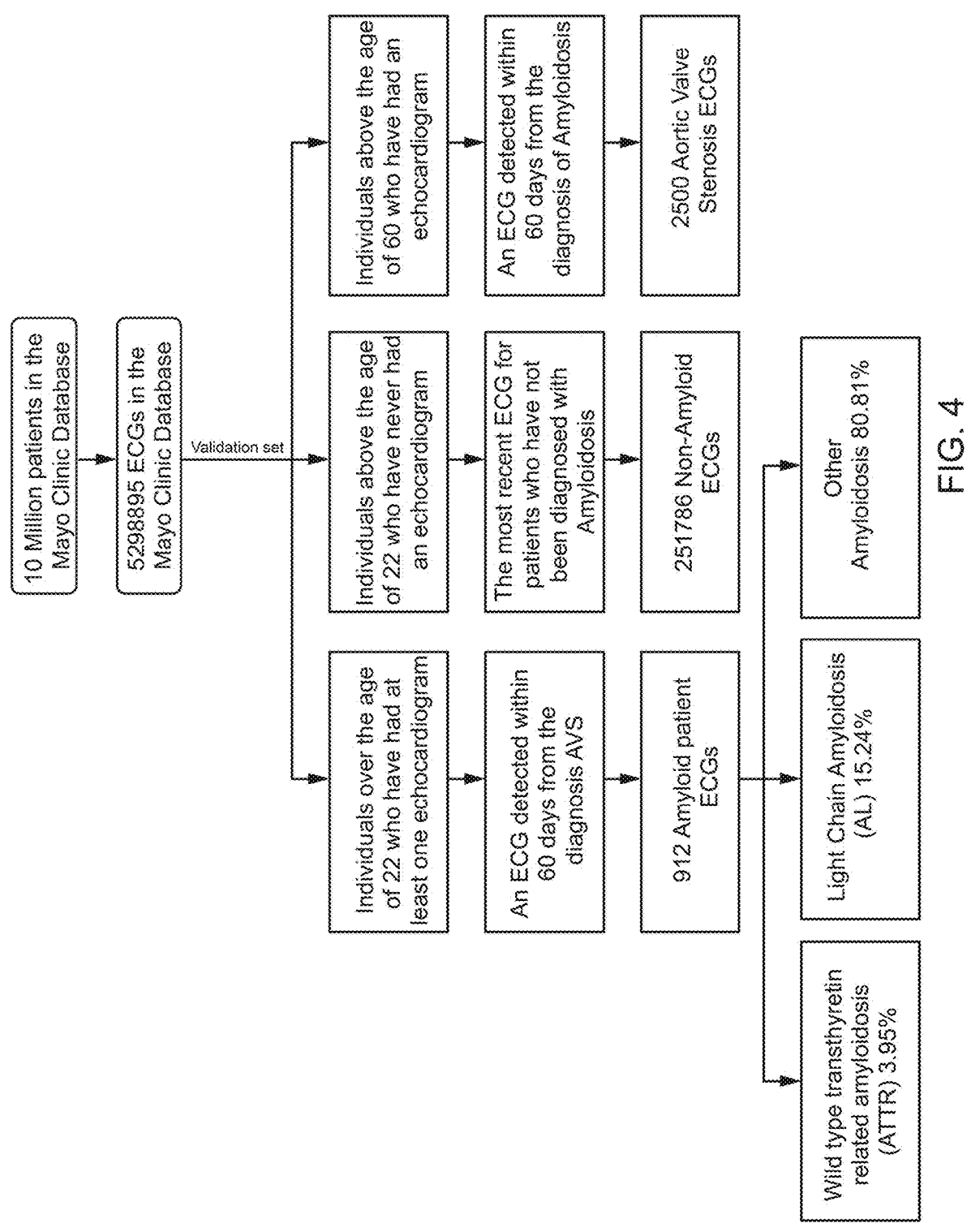
FIG. 4 (FIG. 4) depicts a flow chart with illustrative steps for validation of the data set.

The creation of this dataset serves as a valuable resource for identifying patients who may be concurrently afflicted with aortic stenosis and cardiac amyloidosis. Given that both conditions can share certain clinical symptoms and manifestations, the availability of this dataset provides a unique opportunity to explore potential dual pathologies and enhance the diagnostic accuracy and treatment strategies for patients facing these complex health challenges. FIG. 4 is a flow chart illustrating steps for the creation of the validation dataset.

Table 5 (below) provides an overview of the patient demographics within the Validation dataset. A sample of 255198 was collected for validation. In this dataset 48% of the patients were identified as male and 51.48% as female. The data collection process spanned through all the mayo hospitals including Rochester, Arizona, Florida, and mayo clinic hospital system (MCHS).

In the validation dataset of patients with amyloidosis, the gender distribution reflects a predominance of male patients, constituting 66% of the group, while female patients make-up the remaining 33%. The average age among these individuals stands at 64 years. Notably, a significant proportion of this cohort, specifically 89.91%, belongs to the white ethnicity.

Conversely, the control group with no echocardiogram exhibits a distinct demographic profile. Within this group, male individuals account for 48% of the cases, and female individuals make up 51%, creating a more balanced gender distribution compared to the amyloidosis cohort. The average age of individuals in the control group is notably lower, averaging 55 years. Also, the control group consists predominantly of individuals belonging to the white ethnicity, with 89%.

The second control group comprises individuals diagnosed with aortic valve stenosis. Within this group, there is a notable gender distribution, with males making up 55% of the cases and females comprising the remaining 45%. The overwhelming majority of this control group, specifically 96%, belongs to the white ethnicity.

2.4 Results

The algorithm performed well in identifying amyloid in the validation data sets. The validation process was meticulously executed on two distinct subsets of amyloidosis cases: the first encompassed a comprehensive assessment of individuals with full-blown amyloidosis, while the second subset was specifically dedicated to individuals with cardiac amyloidosis, which can be further categorized into ATTR and AL amyloidosis.

During the initial phase of validation, a comprehensive range of amyloidosis cases was scrutinized, ensuring a thorough assessment of all individuals with this medical condition. The primary objective here was to comprehensively understand and validate the model's performance across the broader spectrum of amyloidosis cases.

Similarly, the results were consistent across all amyloidosis types versus non-echocardiogram patients, revealing an impressive Area Under the Curve (AUC) of 99.4, with a 95% Confidence Interval (CI) spanning from 99.93 to 99.95. This underscores the system's robust and reliable performance in distinguishing amyloidosis cases, irrespective of the specific subtype, from control group.

In the subsequent phase of the validation process, the focus shifted toward a more detailed examination of cardiac amyloidosis, delving into the categorization of this condition into two distinct forms: ATTR and AL amyloidosis. This meticulous separation allowed for a deeper exploration of the model's accuracy and its capacity to differentiate between the various presentations of cardiac amyloidosis. The insights gained from this analysis hold significant clinical relevance, aiding in more precise diagnostic and treatment decision-making.

TABLE 5

| | All | Amyloidosis | | Non-Amyloidosis | |
|---|---|---|---|---|---|
| Total | 255198 | 912 | | 2500 | 251786 |
| Gender | | | | | |
| Male | 123821 (48.52%) | 604 (66.23%) | 1367 (54.68%) | 121850 (48.39%) | |
| Female | 131371 (51.48%) | 308 (33.77%) | 1133 (45.32%) | 129930 (51.60%) | |
| Unknown | — | — | — | <10 | |
| Non- Binary | — | — | — | <10 | |
| AGE | 65.03 | 64.94 | 74.5 | 55.64 | |
| (Mean) | | | | | |
| 22-60 | 145688 (57.09%) | 297 (32.57%) | — | 145391 (57.74%) | |
| 61-70 | 61069 (23.93%) | 318 (34.87%) | 922 (36.88%) | 59829 (23.76%) | |
| 71-80 | 36059 (14.13%) | 231 (25.33%) | 922 (36.88%) | 34906 (13.86%) | |
| 81+ | 12382 (4.85%) | 66 (7.24%) | 656 (26.24%) | 11660 (4.63%) | |
| RACE | | | | | |
| White | 228442 (89.52%) | 820 (89.91%) | 2409 (96.36%) | 225213 (89.45%) | |
| Black | 10151 (3.98%) | 48 (5.26%) | 28 (1.12%) | 10075 (4.00%) | |
| Asian | 11412 (4.47%) | 11 (1.21%) | 20 (0.80%) | 11381 (4.52%) | |
| Others | 5193 (2.03%) | 33 (3.62%) | 43 (1.72%) | 5117 (2.03%) | |

2.3 Model Performance

A sample size of 255198 ECG data was used for validation. The model was evaluated at one or more operating points selected from the development data with equal sensitivity and specificity. These thresholds were applied to the validation data sets to characterize the sensitivity and specificity of the algorithm. Exact 95% confidence intervals were used for all measures of diagnostic performance except for AUC. The confidence interval for AUC was determined based on Sun and Su optimization of the Delong method.

Specifically, when assessing the algorithm's performance in distinguishing Light Chain Amyloidosis from control patients, the results were noteworthy with Area Under the Curve (AUC) of 99.94. The accompanying 95% Confidence Interval (CI) ranged from 99.92 to 99.95, underscoring the algorithm's robust and consistent ability to identify Light Chain Amyloidosis cases. Similarly, in the context of wild-type transthyretin related amyloidosis versus non-echocardiogram patients, the algorithm exhibited an exceptional AUC of 99.95, accompanied by a 95% Confidence Interval (CI) spanning from 99.93 to 99.96. These findings highlight the algorithm's exceptional performance in accurately distinguishing between different forms of cardiac amyloidosis.

In the second control group, individuals diagnosed with aortic valve stenosis were compared to those with amyloidosis. In this comparison, the model exhibited an impressive Area Under the Curve (AUC) of 99.9. The 95% Confidence Interval (CI) associated with this performance metric ranged from 99.8 to 99.97. These results underscore the model's exceptional accuracy in distinguishing between individuals with aortic valve stenosis and those with amyloidosis. This result serves as a valuable resource for identifying patients who may be concurrently afflicted with aortic stenosis and cardiac amyloidosis.

Table 6 summarizes validation data set performance for Amyloidosis.

TABLE 6

| | SE | SP | PPV | NPV | AUC | Accuracy |
|---|---|---|---|---|---|---|
| | | | Amyloid vs AVS | | | |
| Result | 100.0 | 96.72 | 91.75 | 100.0 | 99.9 | 97.60% |
| | (100.0- | (96.02- | (90.04- | (100.0- | (99.8- | |
| | 100.0) | 97.42) | 93.46) | 100.0) | 99.97) | |
| SE = SP | 99.34 | 99.24 | 97.95 | 99.76 | 99.29 | 99.27% |
| | (98.82- | (98.9- | (97.03- | (99.57- | (98.97- | |
| | 99.87) | 99.58) | 98.86) | 99.95) | 99.59) | |
| | | | All Amyloid vs non-Echo | | | |
| Result | 100.0 | 98.75 | 22.42 | 100.0 | 99.94 | 98.75% |
| | (100.0- | (98.7- | (21.14- | (100.0- | (99.93- | |
| | 100.0) | 98.79) | 23.71) | 100.0) | 99.95) | |
| SE = SP | 99.56 | 99.59 | 47.1 | 100.0 | 99.58 | 99.59% |
| | (99.13- | (99.57- | (44.87- | (100.0- | (99.35- | |
| | 99.99) | 99.62) | 49.32) | 100.0) | 99.75) | |
| | | | Light Chain Amyloidosis vs non-Echo | | | |
| Result | 100.0 | 98.75 | 4.22 | 100.0 | 99.94 | 98.75% |
| | (100.0- | (98.7- | (3.53- | (100.0- | (99.92- | |
| | 100.0) | 98.79) | 4.91) | 100.0) | 99.95) | |
| SE = SP | 99.28 | 99.53 | 10.43 | 100.0 | 99.4 | 99.53% |
| | (97.88- | (99.5- | (8.78- | (100.0- | (98.63- | |
| | 100.69) | 99.56) | 12.08) | 100.0) | 99.77) | |
| | | | Wild type transthyretin related amyloidosis vs non-Echo | | | |
| Result | 100.0 | 98.75 | 1.13 | 100.0 | 99.95 | 98.75% |
| | (100.0- | (98.7- | (0.76- | (100.0- | (99.93- | |
| | 100.0) | 98.79) | 1.49) | 100.0) | 99.96) | |
| SE = SP | 100.0 | 99.8 | 6.57 | 100 | 99.9 | 99.80% |
| | (100.0- | (99.78- | (4.5- | (100.0- | (99.89- | |
| | 100.0) | 99.81) | 8.64) | 100.0) | 99.91) | |

Results

Figure 5:
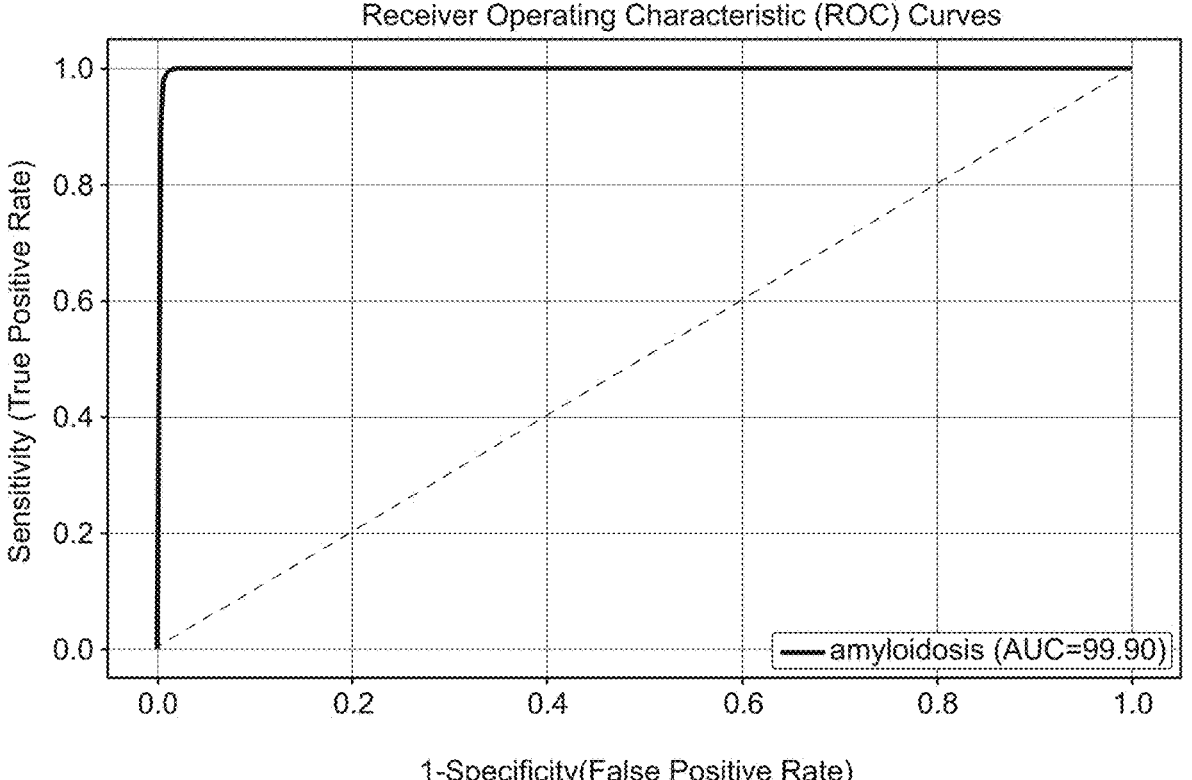
FIG. 5 (FIG. 5) depicts a receiver operating characteristic (ROC) curve for test cases (amyloid vs AVS). The Y-axis represents the sensitivity (true positive rate). The X-axis represents the specificity (false positive rate).

When we evaluate the system's performance using the operating point characterized by equal sensitivity and specificity, the results for each case study are as follows:

In the context of distinguishing Amyloidosis from Aortic Valve Stenosis (AVS), the network achieved a high sensitivity of 99.34% (with a 95% Confidence Interval (CI) spanning from 98.82% to 99.87%). This indicates that the network accurately identifies a vast majority of Amyloidosis cases in this comparison. Additionally, it exhibited a commendable specificity of 99.24% (with a 95% CI ranging from 98.9% to 99.58%). This level of specificity ensures that the network minimizes the misclassification of cases, confirming that the majority of AVS cases are correctly recognized as well. These results highlight the network's robust and reliable performance in differentiating between Amyloidosis and Aortic Valve Stenosis. FIG. 5 depicts a receiver operating characteristic (ROC) curve for test cases (amyloid vs AVS). The Y-axis represents the sensitivity (true positive rate). The X-axis represents the specificity (false positive rate).

Figure 6:
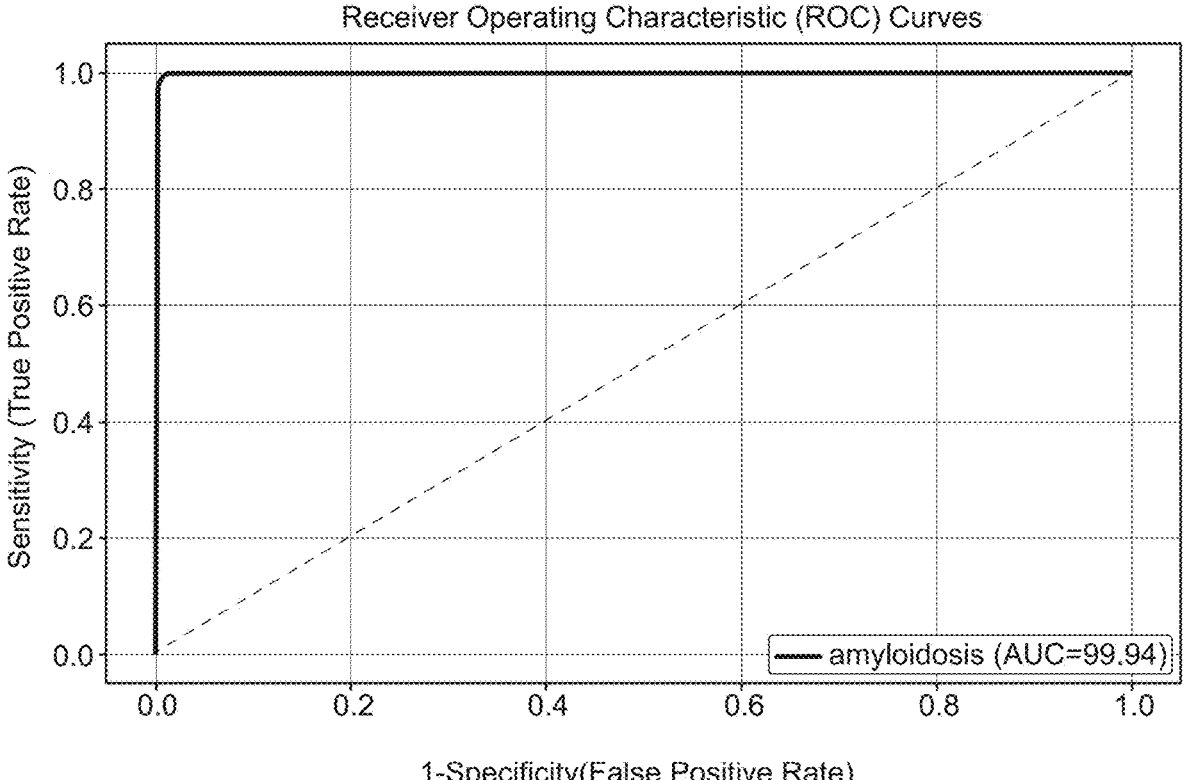
FIG. 6 (FIG. 6) depicts a receiver operating characteristic (ROC) curve for test cases (amyloid vs non-amyloid). The Y-axis represents the sensitivity (true positive rate). The X-axis represents the specificity (false positive rate).

In the case of distinguishing wild type transthyretin-related amyloidosis from non-echocardiogram patients, the network achieved a perfect sensitivity of 100% (with a 95% CI of 100%) and a specificity of 99.8% (with a 95% CI spanning from 99.78% to 99.81%). These outcomes highlight the network's ability to correctly identify cases of wild type transthyretin-related amyloidosis, coupled with a remarkably high specificity that ensures minimal misclassification of non-echocardiogram patients. FIG. 6 depicts a receiver operating characteristic (ROC) curve for test cases (amyloid vs non-Echo). The Y-axis represents the sensitivity (true positive rate). The X-axis represents the specificity (false positive rate).

Figure 7:
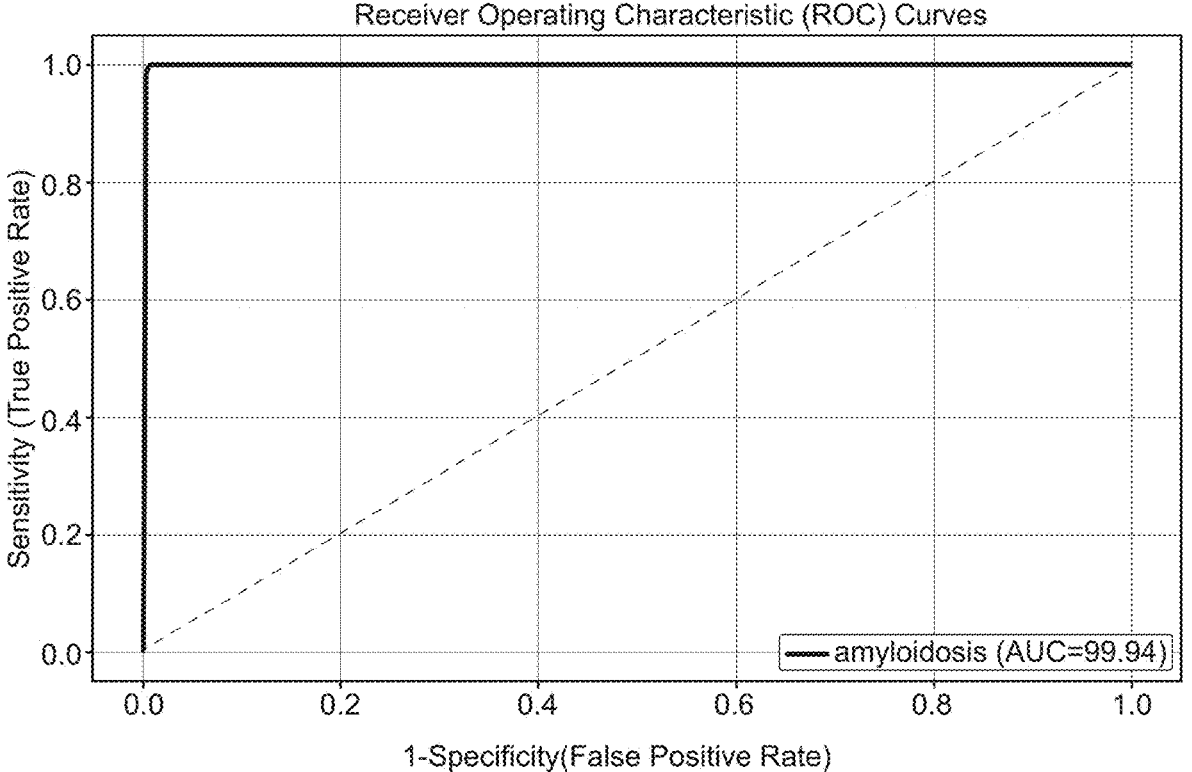
FIG. 7 (FIG. 7) depicts a receiver operating characteristic (ROC) curve for test cases (AL vs non-amyloid). The Y-axis represents the sensitivity (true positive rate). The X-axis represents the specificity (false positive rate).

When assessing the network's performance in recognizing Light Chain Amyloidosis among non-echocardiogram patients, the disclosed systems and methods exhibited a sensitivity of 99.28% (with a 95% CI extending from 97.88% to 100.69%) and a specificity of 99.53% (with a 95% CI in the range of 99.5% to 99.56%). These results underline the network's high accuracy in detecting cases of Light Chain Amyloidosis, assuring that a substantial majority of such cases are correctly identified, while minimizing false positives. FIG. 7 depicts a receiver operating characteristic (ROC) curve for test cases (AL vs non-Echo). The Y-axis represents the sensitivity (true positive rate). The X-axis represents the specificity (false positive rate).

Figure 8:
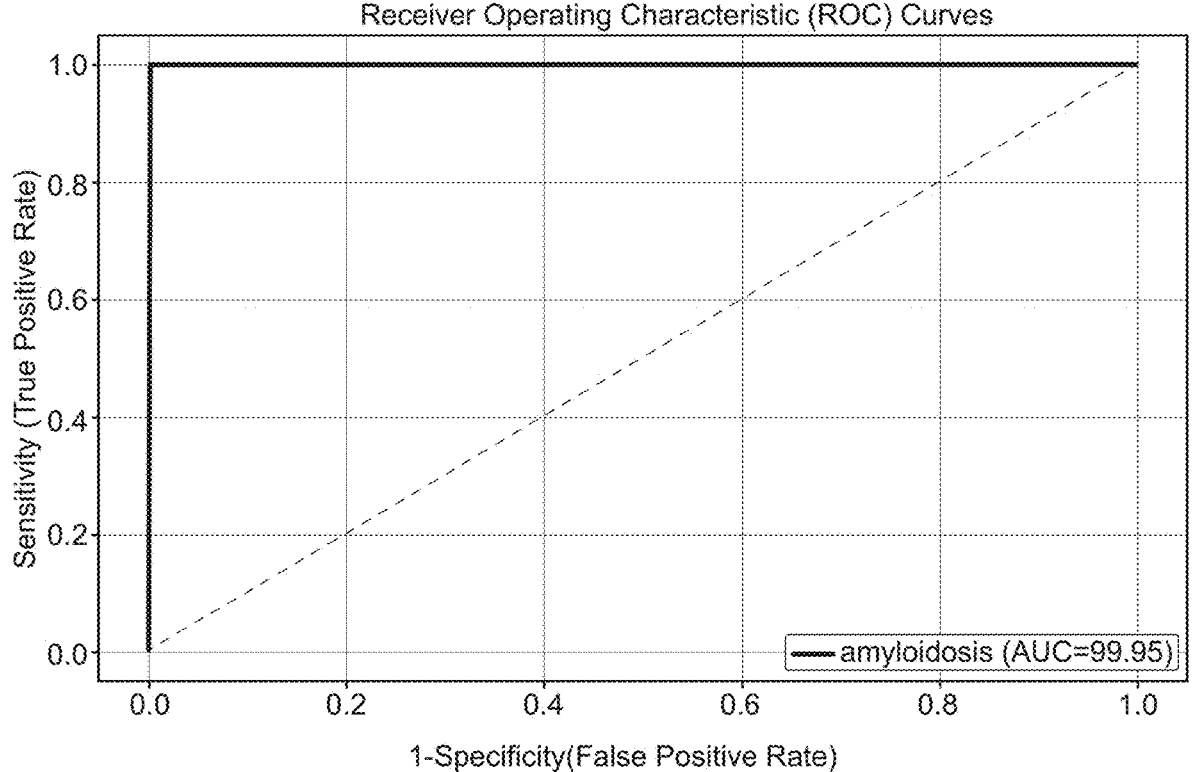
FIG. 8 (FIG. 8) depicts a receiver operating characteristic (ROC) curve for test cases (ATTR vs non-amyloid). The Y-axis represents the sensitivity (true positive rate). The X-axis represents the specificity (false positive rate).

In the context of distinguishing all types of amyloidosis from non-echocardiogram patients, the network demonstrated a remarkable sensitivity of 99.56% (with a 95% Confidence Interval (CI) spanning from 99.13% to 99.99%) and an equally impressive specificity of 99.59% (with a 95% CI ranging from 99.57% to 99.62%). These findings reflect the network's exceptional ability to correctly identify individuals with amyloidosis and those without, maintaining a finely balanced trade-off between sensitivity and specificity. FIG. 8 depicts a receiver operating characteristic (ROC) curve for test cases (ATTR vs non-Echo). The Y-axis represents the sensitivity (true positive rate). The X-axis represents the specificity (false positive rate).

The number of false-positive, false-negative, true-positive, and true-negative results for each model, as well as accuracy, is presented in Table 7. Table 7 is a confusion matrix for amyloidosis validation.

TABLE 7

| | TP | TN | FP | FN | Accuracy |
|---|---|---|---|---|---|
| | | Amyloid vs AVS | | | |
| Result | 912 | 2418 | 82 | 0 | 97.60% |
| SE = SP | 906 | 2481 | 19 | 6 | 99.27% |
| | | All Amyloid vs Control | | | |
| Result | 912 | 248631 | 3155 | 0 | 98.75% |
| SE = SP | 908 | 250766 | 1020 | 4 | 99.59% |
| | | Light Chain Amyloidosis vs Control | | | |
| Result | 139 | 248631 | 3155 | 0 | 98.75% |
| SE = SP | 138 | 250601 | 1185 | 1 | 99.53% |
| | | Wild type transthyretin related amyloidosis vs Control | | | |
| Result | 36 | 248631 | 3155 | 0 | 98.75% |
| SE = SP | 36 | 251274 | 512 | 0 | 99.80% |

Conclusion

The present disclosure identified critical novel features that can be applied for the detection of cardiac amyloidosis from one or more ECG signals. In conclusion, the feedforward neural network of the described systems, meticulously trained and evaluated with careful input from the inventors, has demonstrated exceptional performance in predicting and distinguishing amyloidosis. The validation process, which included assessments of different forms of amyloidosis and their differentiation from non-echocardiogram patients, showcased the network's remarkable accuracy. Its operating point, characterized by balanced sensitivity and specificity, consistently delivered high precision across these case studies.

Notably, the network's ability to identify all types of amyloidosis, Light Chain Amyloidosis, and Wild type transthyretin-related amyloidosis exhibited impressive sensitivity and specificity, offering valuable support for clinical diagnosis. Moreover, the network's capability to discriminate Amyloidosis from Aortic Valve Stenosis further emphasized its reliability and accuracy in complex medical scenarios.

While this invention is satisfied by configurations in many different forms, as described in detail in connection with preferred configurations of the invention, it is understood that the present disclosure is to be considered as exemplary of the principles of the invention and is not intended to limit the invention to the specific configurations illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, 16.

What is claimed is:

1. A computer-implemented method for identifying one or more electrocardiogram (ECG) parameters(s) that are informative of cardiac amyloidosis and generating a diagnostic classification, comprising:

annotating a plurality of electrocardiogram (ECG) parameters in a database as associated with a cardiac amyloidosis designation or a negative cardiac amyloidosis control designation, wherein annotating comprises labeling a plurality of electrocardiograms with one or more cardiac amyloidosis designation, wherein the cardiac amyloidosis designation encompasses cases labeled with one or more of: light chain (AL) amyloidosis, transthyretin related (ATTR) amyloidosis, organ limited amyloidosis, lichen amyloidosis, heredofamilial amyloidosis, unspecified amyloidosis, neuropathic heredofamilial amyloidosis, and secondary systemic amyloidosis;

instructing a machine learning model to distinguish the plurality of electrocardiogram (ECG) parameters, wherein the machine learning model is instructed to distinguish one or more parameters selected from a group comprising a P wave duration, a P wave amplitude, an R wave duration, an R wave amplitude, an S wave amplitude, a T wave duration, a T wave amplitude, a PR Interval (PRI) value, and a QT value based on a pattern present in the one or more cardiac amyloidosis designation that is not present in the negative cardiac amyloidosis control by training the machine learning model on the annotated electrocardiograms to identify patterns distinguishing each of the eight amyloidosis subtypes from negative controls;

applying a SHAP analysis to the plurality of distinguished electrocardiogram (ECG) parameters, wherein applying the SHAP analysis comprises computing a numeric value for each parameter that represents the contribution of that parameter to the distinction between cardiac amyloidosis designations and negative controls, thereby providing a numeric value that represents the contribution of each parameter to the one or more cardiac amyloidosis designation and identifies one or more electrocardiogram (ECG) parameters(s) that are informative of cardiac amyloidosis.

2. The method of claim 1, wherein the P wave duration corresponds to the P wave duration in lead I, the P wave duration in lead II, or the P wave duration in lead III.

3. The method of claim 1, wherein the P wave duration corresponds to the P wave duration in lead $V_1$, the P wave duration in lead $V_2$, the P wave duration in lead $V_3$, the P wave duration in lead $V_4$, the P wave duration in lead $V_5$, or the P wave duration in lead $V_6$.

4. The method of claim 1, wherein the P wave duration corresponds to the P wave duration in lead aVF, the P wave duration in lead aVR, or the P wave duration in lead aVL.

5. The method of claim 1, wherein the P wave amplitude corresponds to the P wave amplitude in lead I, the P wave amplitude in lead II, or the P wave amplitude in lead III.

6. The method of claim 1, wherein the P wave amplitude corresponds to the P wave amplitude in lead $V_1$, the P wave amplitude in lead $V_2$, the P wave amplitude in lead $V_3$, the P wave amplitude in lead $V_4$, the P wave amplitude in lead $V_5$, or the P wave amplitude in lead $V_6$.

7. The method of claim 1, wherein the P wave amplitude corresponds to the P wave amplitude in lead aVF, the P wave amplitude in lead aVR, or the P wave amplitude in lead aVL.

8. The method of claim 1, wherein the R wave duration corresponds to the R wave duration in lead I, the R wave duration in lead II, or the R wave duration in lead III.

9. The method of claim 1, wherein the R wave duration corresponds to the R wave duration in lead $V_1$, the R wave duration in lead $V_2$, the R wave duration in lead $V_3$, the R wave duration in lead $V_4$, the R wave duration in lead $V_5$, or the R wave duration in lead $V_6$.

10. The method of claim 1, wherein the R wave duration corresponds to the R wave duration in lead aVF, the R wave duration in lead aVR, or the R wave duration in lead aVL.

11. The method of claim 1, wherein the R wave amplitude corresponds to the R wave amplitude in lead I, the R wave amplitude in lead II, or the R wave amplitude in lead III.

12. The method of claim 1, wherein the R wave amplitude corresponds to the R wave amplitude in lead $V_1$, the R wave amplitude in lead $V_2$, the R wave amplitude in lead $V_3$, the R wave amplitude in lead $V_4$, the R wave amplitude in lead $V_5$, or the R wave amplitude in lead $V_6$.

13. The method of claim 1, wherein the R wave amplitude corresponds to the R wave amplitude in lead aVF, the R wave amplitude in lead aVR, or the R wave amplitude in lead aVL.

14. The method of claim 1, wherein the S wave amplitude corresponds to the S wave amplitude in lead I, the S wave amplitude in lead II, or the S wave amplitude in lead III.

15. The method of claim 1, wherein the S wave amplitude corresponds to the S wave amplitude in lead $V_1$, the S wave amplitude in lead $V_2$, the S wave amplitude in lead $V_3$, the S wave amplitude in lead $V_4$, the S wave amplitude in lead $V_5$, or the S wave amplitude in lead $V_6$.

16. The method of claim 1, wherein the S wave amplitude corresponds to the S wave amplitude in lead aVF, the S wave amplitude in lead aVR, or the S wave amplitude in lead aVL.

17. The method of claim 1, wherein the T wave amplitude corresponds to the T wave amplitude in lead I, the T wave amplitude in lead II, or the T wave amplitude in lead III.

18. The method of claim 1, wherein the T wave amplitude corresponds to the T wave amplitude in lead $V_1$, the T wave amplitude in lead $V_2$, the T wave amplitude in lead $V_3$, the T wave amplitude in lead $V_4$, the T wave amplitude in lead $V_5$, or the T wave amplitude in lead $V_6$.

19. The method of claim 1, wherein the T wave amplitude corresponds to the T wave amplitude in lead aVF, the T wave amplitude in lead aVR, or the T wave amplitude in lead aVL.

20. The method of claim 1, wherein the PR interval is a value in lead I, wherein the PR interval is a value in lead II, or wherein the PR interval is a value in lead III.

21. The method of claim 1, wherein the PR interval is a value in lead $V_1$, a value in lead $V_2$, a value in lead $V_3$, a value in lead $V_4$, a value in lead $V_5$, or a value in lead $V_6$.

22. The method of claim 1, wherein the PR interval is a value in lead aVF, wherein the PR interval is a value in lead aVL, or wherein the PR interval is a value in lead aVR.

23. The method of claim 1, wherein the machine learning model is a feed forward model.

24. The method of claim 1, wherein the machine learning model is instructed to distinguish 86 ECG parameters.

25. The method of claim 1, wherein the machine learning model receives measurement matrices of the 86 parameters from the database and produces a parameter output between 0 and 1.

26. A computer-implemented system for detecting cardiac amyloidosis from an electrocardiogram signal(s) and outputting actionable diagnostic classifications, the system comprising:

an input module comprising a processor receiving the electrocardiogram (ECG) signal from an information source and extracting one or more of: an R wave amplitude in lead $V_5$ of the ECG; an S wave amplitude in lead $V_3$ of the ECG; an R wave amplitude in lead aVL; an R wave amplitude in lead $V_6$; an R wave amplitude in lead $V_4$; an R wave amplitude in lead I; an S wave amplitude in lead $V_1$; and an S wave amplitude in lead $V_2$;

an analysis module comprising a trained machine learning model, trained on a plurality of cardiac amyloidosis cases with eight amyloidosis subtype designations, trained to apply logic to identify a cardiac amyloidosis pattern and subtype-specific characteristics in one or more of:

the R wave amplitude in lead Vs of the ECG;

the S wave amplitude in lead $V_3$ of the ECG;

the R wave amplitude in lead aVL;

the R wave amplitude in lead $V_6$;

the R wave amplitude in lead $V_4$;

the R wave amplitude in lead I;

the S wave amplitude in lead $V_1$; and the S wave amplitude in lead $V_2$;

an output module for outputting a binary classification indicative of a cardiac amyloidosis pattern in the ECG signal or a non-cardiac amyloidosis pattern in the ECG signal.

27. The system of claim 26, wherein the analysis module is a feedforward neural network.

28. The system of claim 26, wherein the cardiac amyloidosis is selected from the group consisting of: light chain (AL) amyloidosis, transthyretin related (ATTR) amyloidosis, organ limited amyloidosis, lichen amyloidosis, heredofamilial amyloidosis, unspecified amyloidosis, neuropathic heredofamilial amyloidosis, and secondary systemic amyloidosis.

29. The system of claim 26, wherein the analysis module was trained to apply logic to identify cardiac amyloidosis on 3000 patients.

* * * * *